United States Patent
Clamer et al.

(10) Patent No.: US 11,629,165 B2
(45) Date of Patent: Apr. 18, 2023

(54) MOLECULES FOR TARGETING RIBOSOMES AND RIBOSOME-INTERACTING PROTEINS, AND USES THEREOF

(71) Applicant: Immagina Biotechnology S.r.l., Trento (IT)

(72) Inventors: Massimiliano Clamer, Trento (IT); Luca Minati, Grigno (IT)

(73) Assignee: IMMAGINA BIOTECHNOLOGY S.R.L., Trento (IT)

( * ) Notice: Subject to any disclaimer, the term of this patent is extended or adjusted under 35 U.S.C. 154(b) by 84 days.

(21) Appl. No.: 17/259,088

(22) PCT Filed: Jul. 8, 2019

(86) PCT No.: PCT/IB2019/055802
§ 371 (c)(1),
(2) Date: Jan. 8, 2021

(87) PCT Pub. No.: WO2020/012332
PCT Pub. Date: Jan. 16, 2020

(65) Prior Publication Data
US 2021/0277044 A1    Sep. 9, 2021

(30) Foreign Application Priority Data
Jul. 10, 2018  (IT) .................. 102018000007079

(51) Int. Cl.
*C07H 19/16* (2006.01)
*G01N 33/68* (2006.01)
*C07D 473/34* (2006.01)

(52) U.S. Cl.
CPC .......... *C07H 19/16* (2013.01); *C07D 473/34* (2013.01); *G01N 33/6848* (2013.01)

(58) Field of Classification Search
None
See application file for complete search history.

(56) References Cited

U.S. PATENT DOCUMENTS

| 10,183,955 B2 * | 1/2019 | Clamer | C07D 519/00 |
| 2013/0122535 A1 * | 5/2013 | Salic | C07K 14/003 |
| | | | 536/27.22 |

OTHER PUBLICATIONS

Jingyan GE, et al., "Puromycin Analogues Capable of Multiplexed Imaging and Profiling of Protein Synthesis and Dynamics in Live Cells and Neurons", Newly Synthesized Proteins, Angewandte Chemie International Edition, vol. 55, Jan. 1, 2016, pp. 4933-4937 (5 pages).

International Search Report and Written Opinion of the ISA for PCT/IB2019/055802 dated Oct. 28, 2019, 9 pages.

\* cited by examiner

*Primary Examiner* — Traviss C McIntosh, III
(74) *Attorney, Agent, or Firm* — Nixon & Vanderhye P.C.

(57) ABSTRACT

Molecule having the structural formula (I): (I) for use as targeting probe of translating ribosomes and ribosome-interacting proteins.

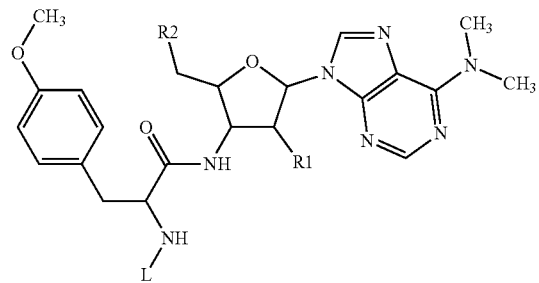

26 Claims, 22 Drawing Sheets a b

MOLECULES FOR TARGETING RIBOSOMES AND RIBOSOME-INTERACTING PROTEINS, AND USES THEREOF

This application is the U.S. national phase of International Application No. PCT/IB2019/055802 filed Jul. 8, 2019 which designated the U.S. and claims priority to IT Patent Application No. 102018000007079 filed Jul. 10, 2018, the entire contents of each of which are hereby incorporated by reference.

FIELD OF THE INVENTION

The present disclosure concerns novel molecules useful for targeting translating ribosomes and ribosome-interacting proteins.

BACKGROUND ART

The ribosome is a dynamic platform that convert genetic information within messenger RNA (mRNA) into a corresponding polypeptide sequence. Many aspects of the translation machinery have been revealed, starting from the characterization of ribosome structure and catalytic activity[1,2] to the organized structure of polyribosomes[3]. At the very beginning of these studies, many antibiotics were used to probe fundamental mechanisms of protein synthesis. Puromycin, an analogue of the 3'-end tyrosylated-tRNA[4,5], is one of the first drug used for these applications. Puromycin participate in the peptide bond formation[6], through the irreversible reaction of the α-amino group with the peptidyl tRNA, causing the release of the nascent peptide and ribosome dissociation all along the transcript[7]. A number of synthetic derivatives have been tested as substrate analogues to probe the ribosome catalytic activity. Some of these studies used puromycin analogs with a stable amide linker on the α-amino group, to control puromycin incorporation in the nascent peptide[8-11]. Nevertheless, the activity of puromycin derivatives outside the mechanistic frame of peptide bond formation has never been tested in details.

SUMMARY OF THE INVENTION

The object of this disclosure is to provide novel molecules able to target translating ribosomes and ribosome-interacting proteins.

According to the invention, the above object is achieved thanks to the subject matter recalled specifically in the ensuing claims, which are understood as forming an integral part of this disclosure.

The instant disclosure concerns novel molecules having the structural formula (I):

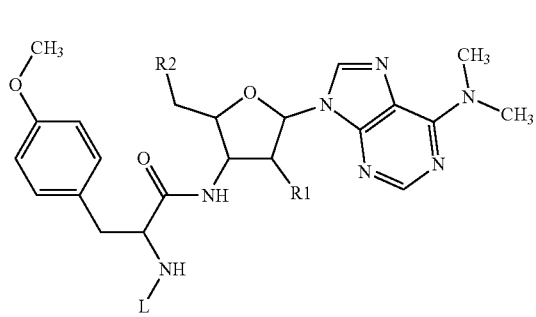

wherein
R1 and R2 are independently selected from

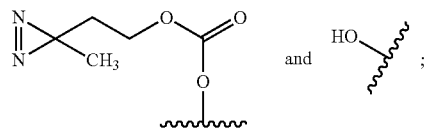

L is selected from

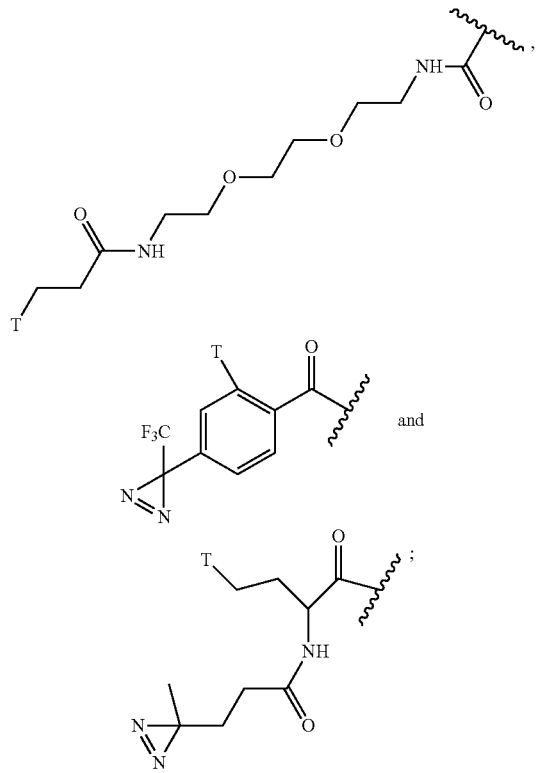

T is selected from

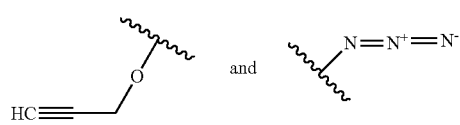

with the proviso that
if R1 is

then R2 is

According to a further embodiment, the instant description discloses the use of the molecule of general formula (I)

for targeting at least one translating ribosome and/or at least one ribosome-interacting protein from a biological sample.

BRIEF DESCRIPTION OF THE DRAWINGS

The invention will now be described in detail, purely by way of illustrative and non-limiting example, with reference to the attached figures, wherein:

FIG. 7. Labelling activity. (a) Immunoblotting of puromycin (top) and actin (bottom) on cytoplasmic protein extracts from HEK-293 cell treated with the probes reported in the table on the left (all probes are used at 50 μM, with 10 min incubation time). UV-treatment: 365 nm, 0.75 J/cm$^2$. Lane 7 reports cells treated with 3PBis without UV-treatment, (b) chemical structure of the probes used in a.

DETAILED DESCRIPTION OF THE INVENTION

Figure 1:
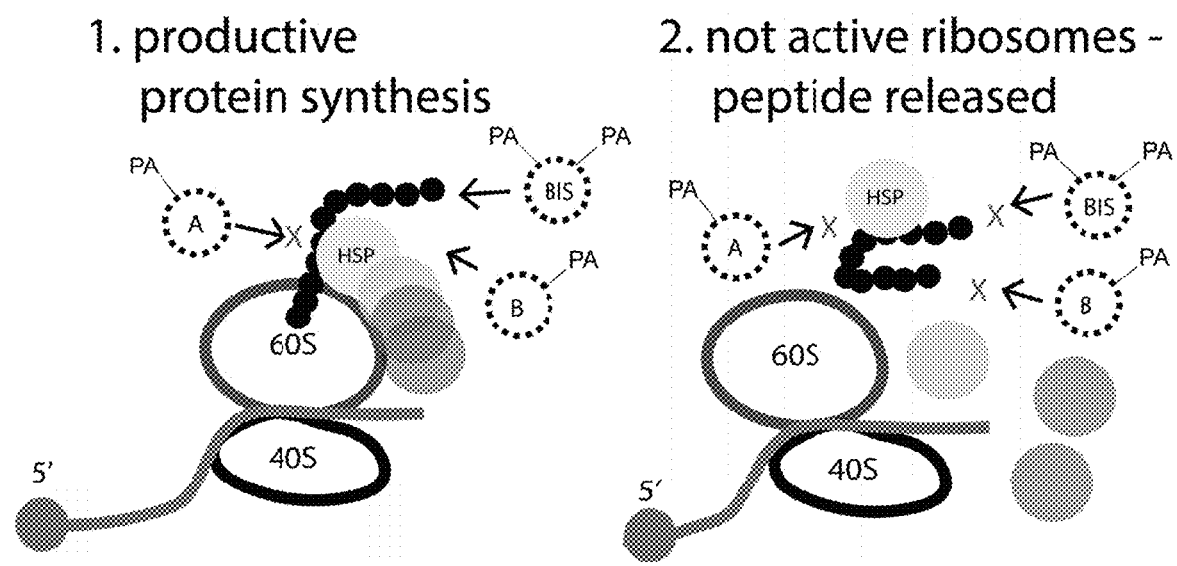
FIG. 1. Proposed model of 3Px binding. PA, photoactive moiety.

In the following description, numerous specific details are given to provide a thorough understanding of embodiments. The embodiments can be practiced without one or more of the specific details, or with other methods, components, materials, etc. in other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The instant disclosure concerns novel molecules having the structural formula (I):

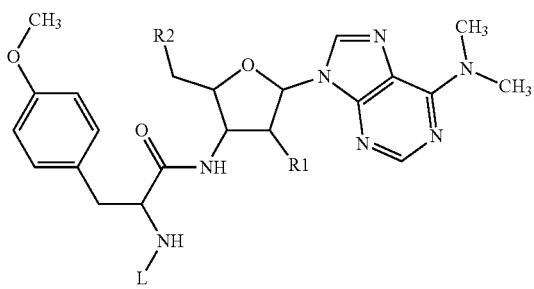

wherein
R1 and R2 are independently selected from

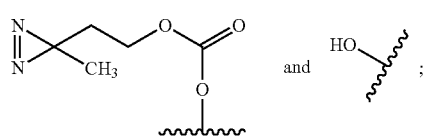

L is selected from

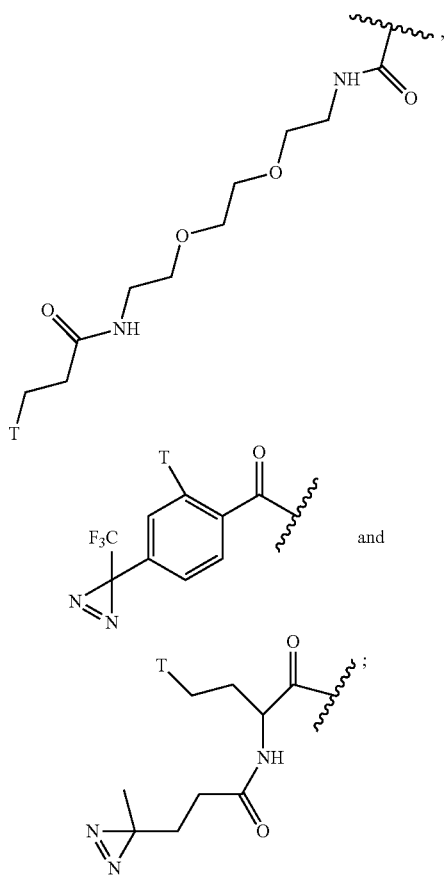

T is selected from

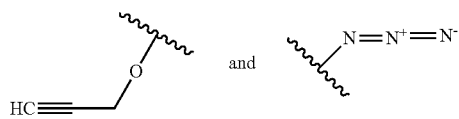

with the proviso that if R1 is

then R2 is

According to one embodiment, R1 is

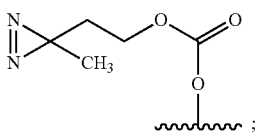

R2 is selected from
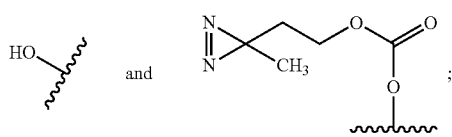
and
L is
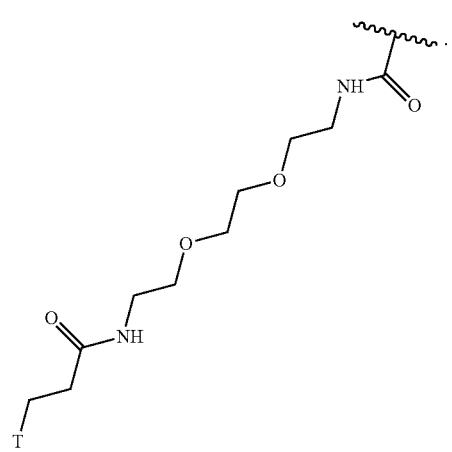
According to one embodiment, R1 is
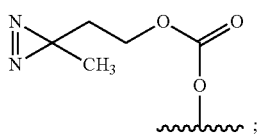 [SMILES: *OC(=O)OCCC1(C)N=N1]
R2 is selected from
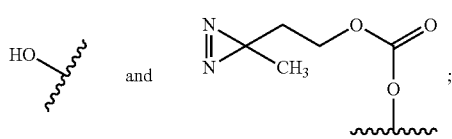
L is
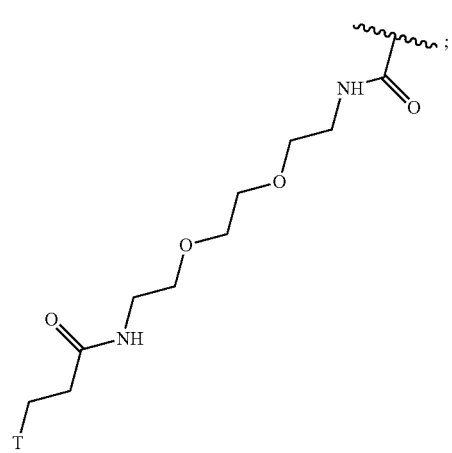
and T is
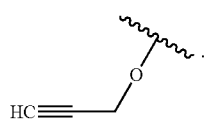
According to a further embodiment, R1 and R2 are
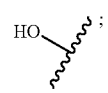
and L is selected from
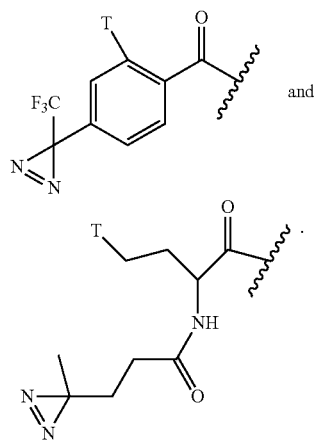
According to a still further embodiment, R1 and R2 are
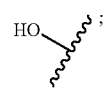
L is
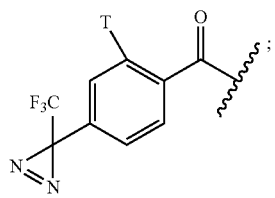
and T is
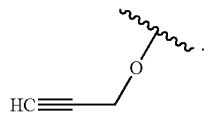
According to a still further embodiment, R1 and R2 are
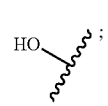

L is

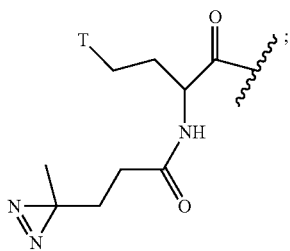

and T is

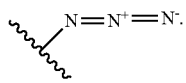

The molecules described herein are useful probes for targeting either a protein associated to a nascent polypeptide emerging, during its translation, from a ribosome and at least one translating ribosome in a biological sample. Preferably, the at least one active ribosome is associated to an RNA, a mRNA, or a protein.

The molecules described herein are useful probes for targeting at least one ribosome-interacting protein in a biological sample.

The molecules described herein are useful adjuvant probes for locking the nascent chain in translating ribosomes.

In a preferred embodiment, the at least one ribosome-interacting protein is selected from the following families: elongation factors, chaperon proteins, ribosomal proteins, proteins involved in cell metabolism, RNA processing proteins, proteins part of the cytoskeleton.

In a preferred embodiment, the ribosome-interacting protein contains an ATPasic site.

In a preferred embodiment, the ribosome-interacting protein belonging to the elongation factors family is selected from: eEF1A, eEF2 and eEF4G.

In a preferred embodiment, the ribosome-interacting protein belonging to the chaperon proteins family is selected from: HSP90AB1, PPIA, HSP5A or isoforms thereof.

In a preferred embodiment, the ribosome-interacting protein belonging to the ribosomal proteins family is RPL18.

In a preferred embodiment, the ribosome-interacting protein belonging to the cell metabolism family is Enol and PHGDH.

In a preferred embodiment, the ribosome-interacting protein belonging to RNA processing proteins family is HNRNPK.

In a preferred embodiment, the ribosome-interacting protein belonging to the cytoskeleton proteins family is Actin or Keratins.

In a still further preferred embodiment, the at least one ribosome-interacting protein is selected from Enol, PHGDH, KRT2, HNRNPK, HSPA5/GRP78 or isoforms thereof.

The biological sample wherein the molecules object of the instant disclosure are used is selected from a cell culture, a cell lysate or a tissue lysate.

The present disclosure shows for the first time that photoreactive puromycin-like probes (3Px) can interact either with proteins cooperating in protein synthesis and translating ribosomes. Overall, these molecules are new valuable tools to monitor protein synthesis and to study translation on the protein-exposed ribosome surface.

Starting from the observation that amino-modified puromycin molecules functionalized with alkyne and diazirine reactive moieties can penetrate cell membrane in vitro and bind selective cytoplasmic protein targets, the present inventors demonstrated that (i) some of these probes can selectively bind ribosome-interacting proteins; (ii) the binding depends on protein synthesis activity; (ii) the probes can be used to monitor effective translation (FIG. 1).

Retaining the puromycin structure in the instant derivatives, allowed the inventors to detect and monitor the presence of puromycin-tag proteins with commercial puromycin antibodies. First, the inventors observed that the position of the UV-active (diazirine moiety) on the puromycin molecule is critical for the binding. Although all the molecules synthetized are resembling the terminal tRNA, modifications are affecting the binding activity: when the UV-active group is placed on the 5'-OH of the ribose (3PA) the molecule is not active, while when the functional group is on the 2'-OH (3PB) or on both 5' and 2'-OH (3PBis) the molecules possess the functional activity. Second, the inventors investigated the conditions that modulate the labelling, showing that the global depression of translation (by arsenite treatment or low serum concentration) is reducing the binding to the target. Third, the inventors examined the affected protein targets. Thanks to the presence of an alkyne/azide affinity handle linked on the α-amino group that enable "click" reaction, the inventors successfully labelled proteins and constitutive ribosomal RNA, with tags (e.g. N3-fluorescent dyes, N3-biotin) for separation of the targets, pull down or fluorescent-based detection experiments.

The present approach allowed to (i) confirm different binding affinity for the targets when protein synthesis is inhibited by puromycin or high concentrations of cycloheximide; (ii) identify and pull-down protein targets. To identify 3PB-binding proteins on a global scale in living cells the inventors applied two strategies. The first based on 3PB-affinity beads pull-down followed by protein digestion; the second based on an in-column "click" binding and digestion of the polypeptides. Combining different data-sets (3PB-targets and control Peg-beads) 15 putative 3PB binders were identified. Most of the proteins are known to be involved with protein synthesis and homeostasis. Among them, the elongation factors eEF1A, eEF2 and eEF4G and chaperon proteins involved in the correct protein folding (HSP5A, HSP90AB1, PPIA) were found. Surprisingly, the inventors identified as enriched only one ribosomal protein (RPL18), which is exposed on the solvent side of the large ribosomal subunit. The inventors identified proteins involved in cell metabolism (e.g. Enol), RNA processing (HNRNPK) and constitutive part of the cytoskeleton (e.g. KR2). Most of these proteins were found to be associated to ribosomes in previous MS-studies[12,13]. Increasing the stringency of the analysis allowed to identify the top-five proteins more enriched in our MS experiments (Enol, HSPA5/GRP78, PHGDH, KRT2, HNRNPK). The inventors focused the attention on the pleiotropic HSPA5/GRP78 protein, because (i) it controls protein synthesis by regulating eIF2α phosphorylation[14,15], (ii) it co-operates for the nascent protein folding and (iii) it is a key player in the regulation of cell proliferation, PI3K/AKT signaling and cell viability[16,17] Curiously, the expression of the protein itself is tight regulated at the translational level[18]. Apart from the endoreticulum (ER), HSPA5/GRP78 is present in other cellular compartments, and the shorter GRP78va isoform is known to reside mainly in the cytosol[19]. By both affinity-pulldown and CuAAC reaction followed by avidin-beads separation, the inventors demonstrated that a HSPA5/GRP78 isoform is a 3PB/3Pbis target.

To better clarify the binding site, an ATP-derived inhibitor of GRP78 (VER-155008) was used to probe the reactivity of 3PB and 3PBis. The present data suggest an antagonist effect of VER-155008 on 3PB binding, indicating a possible common binding site. 3PBis is not affected at the condition used in this work.

Overall, the present data support a GRP78 isoform as a target of 3PB and 3PBis, wherein the labelled protein can be a truncated variant, a different isoform or a sub-population of post-translationally modified HSPA5/GRP78.

In eukaryotic cells, the network of chaperones that engage nascent chains includes ATP-independent and ATP-dependent Hsp60, Hsp70, and Hsp90 chaperone families[20]. Since HSPA5/GRP78 (a member of the Hsp70 family) is known to coordinate co-translational protein folding, the possible use of these active probes to selectively isolate the translational apparatus (i.e productive ribosomes) was investigated. First, the inventors demonstrated that (i) the short 3PB/3PBis-labelled HSPA5/GRP78 variant has a similar co-sedimentation profile with 3PBis and 3PB, all along the polysome profile, and (ii) HSPA5/GRP78 co-precipitate with ribosomal proteins involved in active translation. Then, the inventors successfully used 3PB-functionalized beads to pull down a GRP78-associated full-length mRNA. These results pave the way for better deep-sequencing analysis of mRNAs or ribosome protected fragments purified from chaperon-nascent chain bound ribosomes[21,22].

Results

Design and Synthesis

Figure 2:
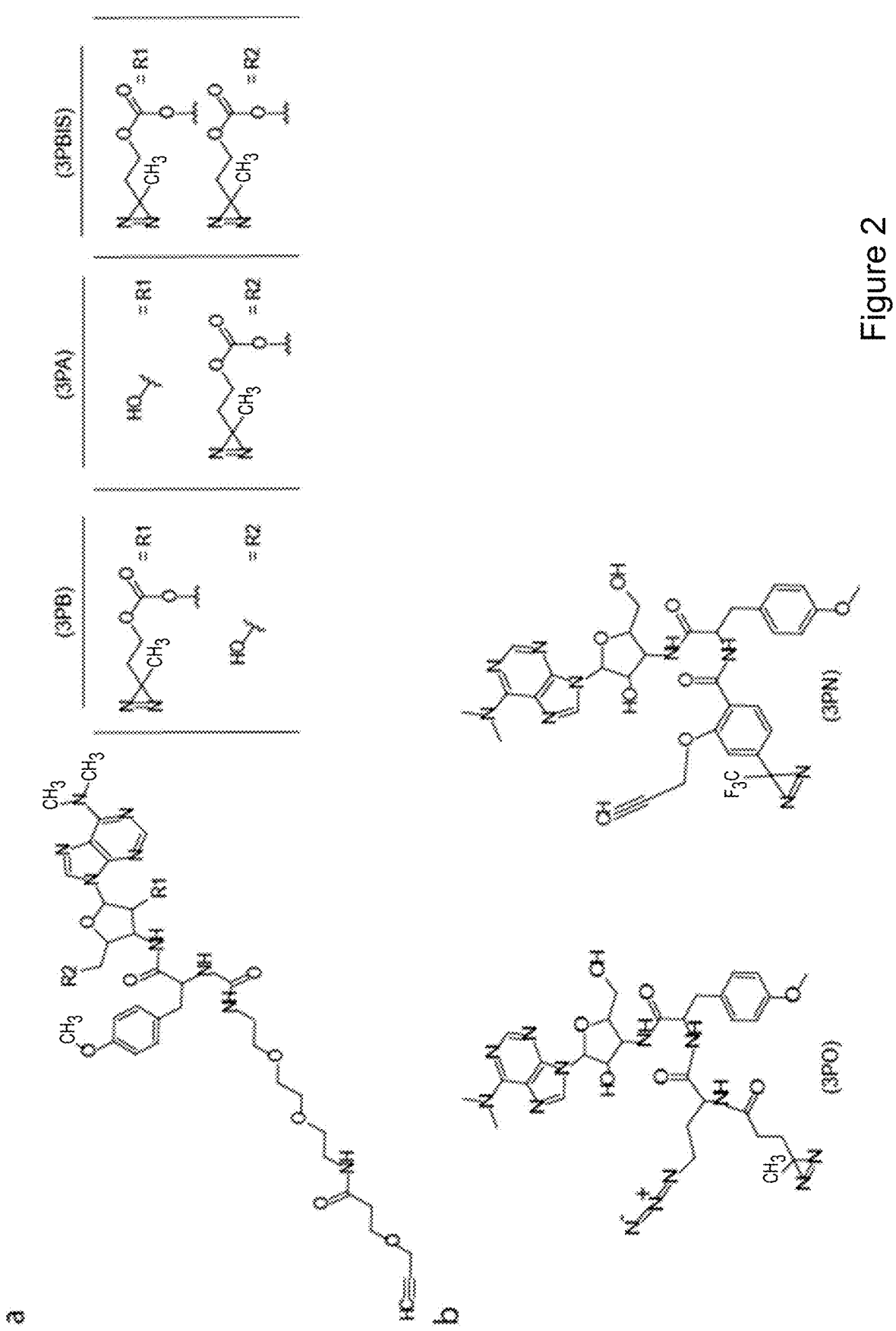
FIG. 2. Chemical structure of the 3Px molecules. (a) 3PB, 3PA and 3PBis molecules: General structure (left) and identity of residues R1 and R2 (right). (b) Chemical structure of 3PO and 3PN molecules.
Figure 3:
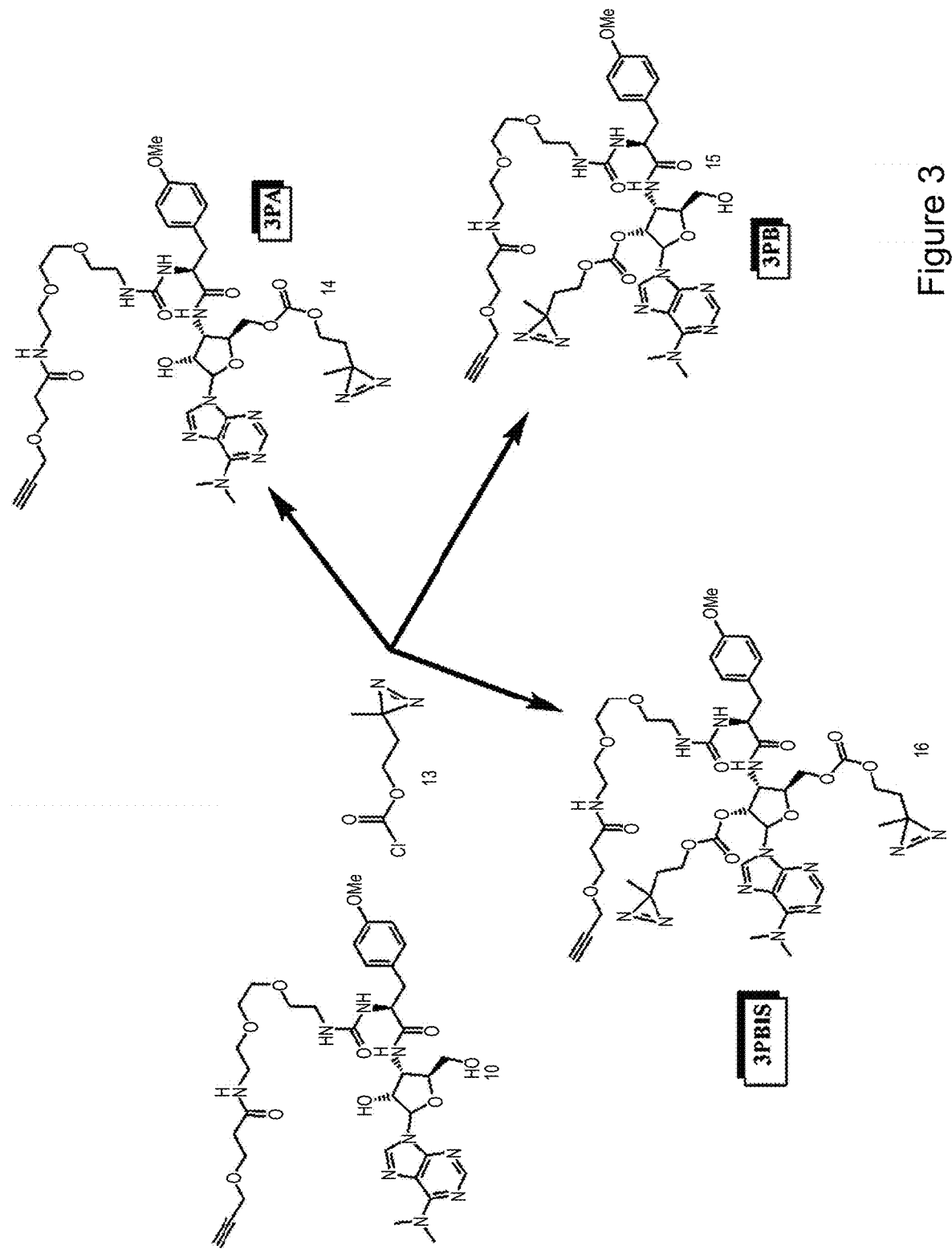
FIG. 3. Final step of 3PA, 3PB and 3PBIS chemical synthesis. Compound 14, 3PA; compound 15, 3PB, compound 16, 3PBis.

In analyzing the effect of puromycin on the ribosomal peptidyl transferase center, we were interested to test if some puromycin derivatives can bind ribosomal RNA, ribosomal proteins or other proteins involved in synthesis of a newly synthetized polypeptide. We infer that, for mapping alternative puromycin binding sites in living cells, the selected probes would need to have four general features: (i) the ability to permeate cell membrane, (ii) a UV-active moiety to covalently bind target proteins or RNA; (iii) a latent affinity handle for downstream labeling[23], and (iv) a conserved puromycin scaffold for immuno-detection of the target. To test this approach, we chemically synthesized five diazirine-alkyne/azide conjugated analogues of puromycin. The alkyne is used to enrich and identify possible targets by copper-catalyzed azide-alkyne cycloaddition (CuAAC[24] or copper catalyzed "click" reaction), while the diazirine moiety on the sugar ring permit covalent protein binding upon UV light (365 nm) irradiation. At the puromycin α-amino group, we linked an alkyne affinity handle through a linker unit. We synthesized five different probes (all together called 3Px), placing the diazirine, in the linker or at the 5'-OH (called 3PA), at the 2'-OH (called 3PB) or at both 2'- and 5'-OH (celled 3PBis) of the ribose respectively (FIGS. 1 and 2). MS and NMR data confirm the final products (FIG. 3 and Methods for the chemical synthesis).

Effect of UV-365 Treatment on the Cells.

Figure 4:
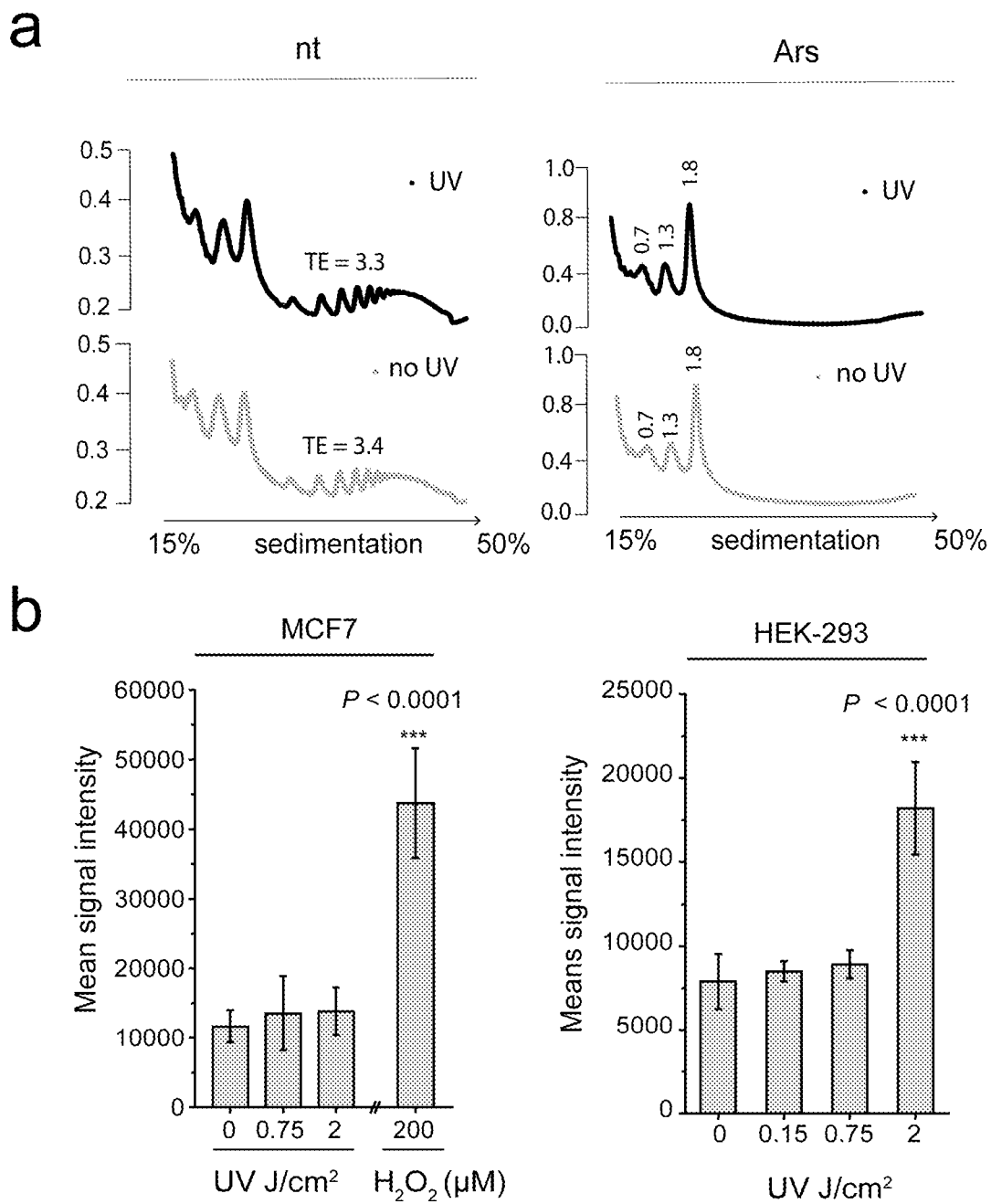
FIG. 4. Effect of UV exposure. (a) Polysome profiles with integrated pick area of MCF7 cells UV-exposed (5 min, 365 nm, 0.75 J/cm$^2$) or non UV-exposed (no UV), without (left) or with (right) arsenite treatment (1 mM, 1 hour). The ratio between the polysomal area and the 80S peak area is reported (indicated as TE, translation efficiency) for the profiles of cells not treated with arsenite; while the area of the 40S, 60S and 80S peaks is reported for the arsenite treated sample (b) Mean fluorescence signal intensity of MCF7 (left) and HEK-293 cells treated with or without UV at the reported total power (BLX-365). MCF7 where also treated with 200 μM hydrogen peroxide as positive control. Cells were stained with Cell ROX Deep Green Reagent to monitor the formation of reactive oxygen species. ***=the values are significantly different from controls with P≤0.0001, One-Way ANOVA, n=50 for each sample.

Before treating cells with the new probes, we defined the UV dose that does not cause damage to our biological models. In order to do that, we monitored the translational impairment and the formation of reactive oxygen species in MCF7 and HEK-293 cells. After irradiation with different energies, no obvious difference in the polysomal profile obtained from MCF7 cells was observed compared to untreated cells (FIG. 4a). In fact, the integrated peak area of 40S, 60S, 80S and polysomes does not change upon irradiation. Moreover, no significant change in reactive oxygen species at up to 0.75 J/cm$^2$ was measured in MCF7 and HEK-293 cells, when compared with the untreated samples (FIG. 4b).

Targeting Profiling in Cells

Figure 5:
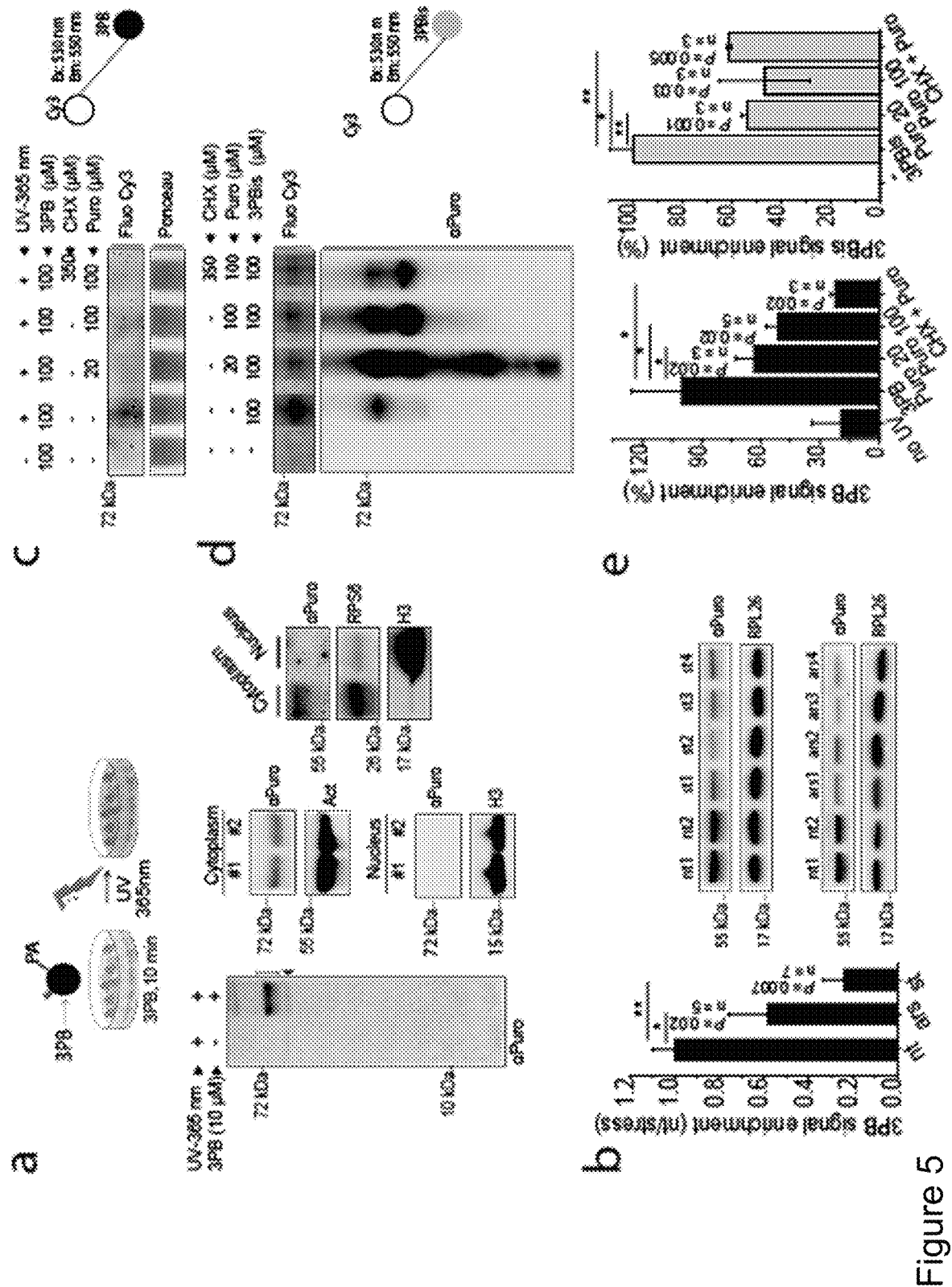
FIG. 5. 3PB and 3PBis protein binding. (a, top) Scheme for cell treatment with 3Px probes. Probes were added to the complete medium and incubated with the cells at 37° C. for 10 minutes. After washing with cold PBS, UV irradiation and cytoplasmic lysis, samples are then processed for further analysis. PA, photoactive moiety. (a, bottom) Immunoblotting with anti-puromycin antibody (αPuro) of a nitrocellulose membrane containing the total protein extract after urea lysis of HEK-293 cell treated or not with 3PB (10 μM, 10 min). Black broken line, main 3PB targets; black arrow, unspecific signal due to the αPuro antibody. On the right, subcellular fractionation and immunoblotting of MCF7 cells treated with 3PB (100 μM, 10 min). Actin (act) RPS6 and Histone 3 (H3) are used as cytoplasmic (Act and RPS6) and nuclear (H3) marker respectively. #, independent replicates. (b) Histogram reporting the quantification of the immunoblots related to the 3PB-tag proteins at about 65 KD treated or not treated with arsenite (1 mM, 1 hour) or 0.5% FBS (18 hours). Representative immunoblots are reported on the right. Numbers are independent replicates. Nt: not treated; ars: arsenite treatment, st: FBS 0.5%. (c) In-gel fluorescent image of total protein extracts from MCF7 cells treated with 3PB (100 μM), with or without 365-nm UV irradiation, and with or without CHX and puromycin at the indicated concentrations. Cell lysates were conjugated to a Cy3-azide reporter by CuAAC and the analysis performed by SDS-PAGE and fluorescence scanning. Ponceau membrane staining of the total protein content is reported below. (d) In-gel fluorescent image of total protein extracts from MCF7 cells treated with 3PBis (100 μM), with or without CHX and puromycin at the indicated concentrations. Cell lysates were conjugated to a Cy3-azide reporter tag by CuAAC and the analysis performed by SDS-PAGE and fluorescence scanning. Immunoblot of puromycin is reported below. (e) Quantification of the 65 KD bands intensity tagged with 3PB (left) or 3PBis (right), with or without UV, and with or without CHX and puromycin added to the cells. Representative images reported in (d). Data are normalized (%) to the 3PB/3PBis treated cells without drugs. 3PB: 100 μM, 10 min; 3PBis: 100 μM, 10 min; Puro 20, 20 μM, 2 hours; Puro 100: 100 μM, 2 hours; CHX+Puro: 100 μM puromycin following 350 μM CHX treatment. Immunoblots were scanned with Typhoon Trio (Ex. max: 530/Em. max: 550) and analysed with ImageJ v1.45s. For all experiments, error bars represent the s.d. of three experiments. t-test P-val reported.
Figure 6:
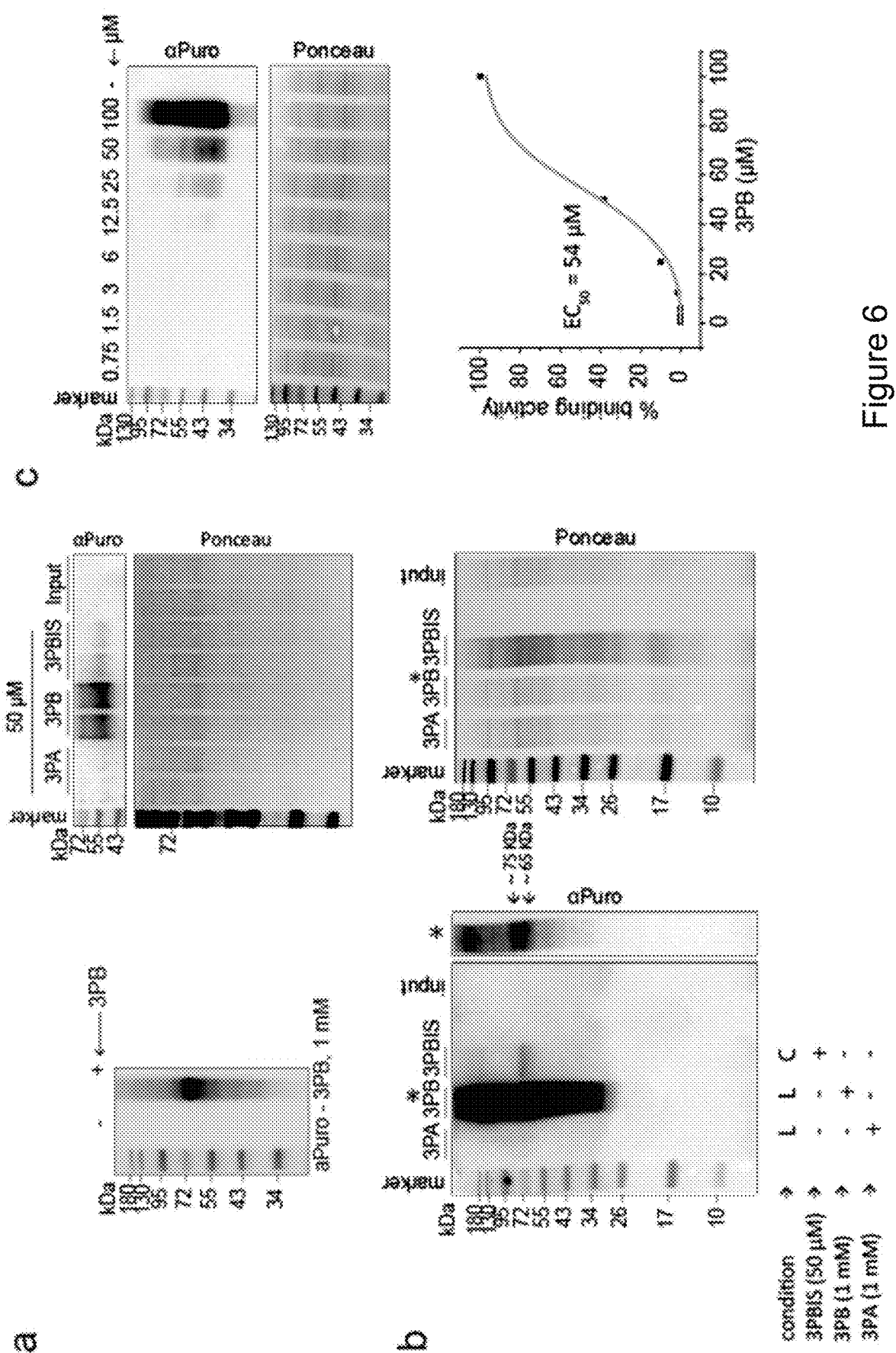
FIG. 6. Reaction before or after cell lysis. (a, left) Immunoblotting with anti-puromycin antibody of a nitrocellulose membrane containing the total protein extract after urea lysis of HEK-293 cell treated or not treated with 3PB (1 mM, 10 min). (a, right) Immunoblotting of puromycin (top) and ponceau staining (bottom) of a nitrocellulose membrane containing cytoplasmic protein extract from HEK-293 cell incubated with 3PA, 3PB or 3PBis (50 μM, 60 min) after UV irradiation. (b) Immunoblot of puromycin (left) and ponceau staining (right) of cytoplasmic protein extracts from HEK-293 cells. Condition "C" (reaction in the cell media): cells were treated with CHX (10 μg/mL, 5 min) and then with 50 μM 3PBIS for 10 min. Condition "L" (reaction in the cell lysate): the cell lysate is incubated for 1 h at 4° C. with 3PBIS (50 mM), 3PA (1 mM) or 3PB (1 mM) and loaded on a SDS-PAGE gel for immunoblotting. Black star: different exposure time of the membrane for the 3PB lane. Arrows: two main bands associated to 3PB at 75 kDa and 65 kDa respectively. (c) Increasing concentration of the 3PBis probe reacted in the cell lysate. (top) puromycin immunoblotting. (bottom) Ponceau staining. (left) Best fit of the data set obtained from the total lane intensity (immunoblot) for each 3PBis concentration. The concentration causing 50% of total binding (EC50) is reported.
Figure 7:
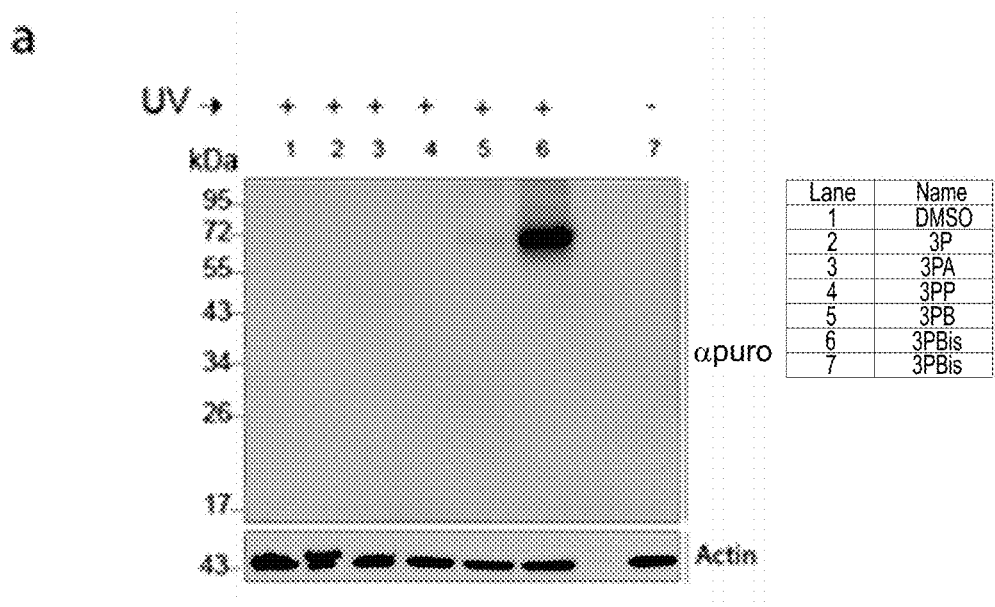
Figure 7:
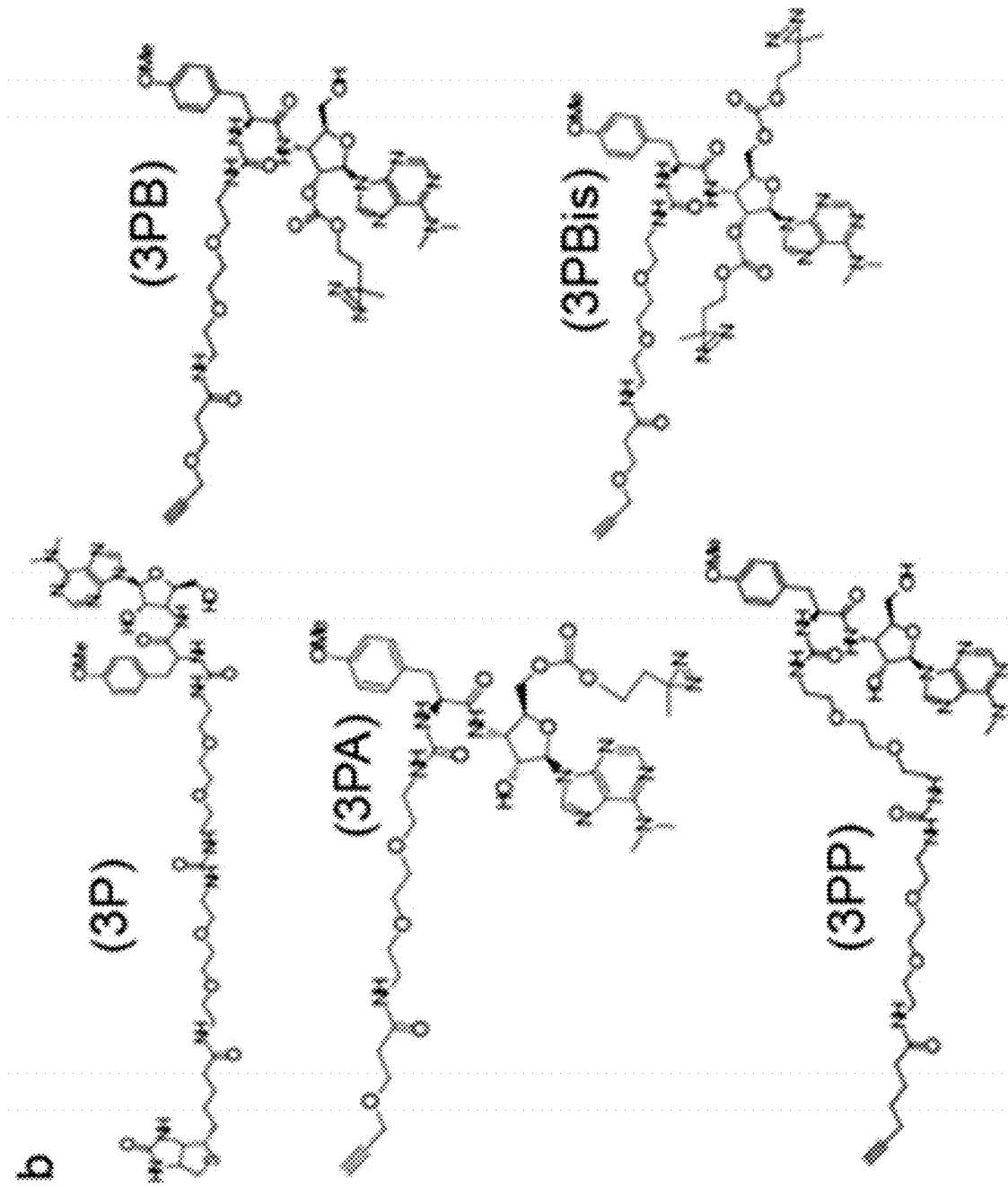

For our initial analysis, we treated HEK-293 and MCF7 cell lines in complete culture medium with the 3PB probe (10 μM) for 10 min, followed by irradiation for 5 min on ice (total power: 0.75 J/cm2). We first assessed 3PB labeling of cellular proteins using SDS-PAGE analysis. Immunoblot with anti-puromycin antibody shows specific puromycin-tag proteins of about 65 kDa, localized in the cytoplasm and not in the nucleus (FIG. 5a). Increasing the concentration to 1 mM generates multiple bands in the immunoblot, indicating that the target specificity is decreasing at higher probe concentrations (FIG. 6a). Then, we compared the labelling activity of 3PB, 3PA and 3PBis in HEK293 and MCF7 cells, adding the probes before or after cell lysis. In the latter case, each probe is incubated for 1 h in the cytoplasmic cell extract at 4° C., followed by UV irradiation (0.75 J/cm$^2$) of the treated lysate. We observed concentration-dependent increases in protein labeling for 3PB and 3PBis (FIG. 6a-c), while no detectable signal from 3PA is observed. Therefore, both 3PB and 3PBis show additional bands with MW=~50 kDa, when reacted in the cell lysate, with respect to the situation when probes are incubated with growing cells (FIG. 6a). Additionally, at high concentration in the cell lysate, 3PB shows main bands at both 75 kDa and 65 kDa (FIG. 6b). Overall, 3PB shows a stronger protein-labeling compared to 3PBis when is incubated with the cell lysate (FIG. 6a-c), but the activity is reduced, respect to 3PBis, when incubated in cell culture. This is presumably due to the higher hydrophobicity of the 3PBis probe and a consequent better cell membrane penetration (FIG. 7). The labeling is UV and diazirino-dependent, as demonstrated by comparative experiments with or without UV treatment, and with similar molecules missing the diazirine tag (FIG. 7).

Figure 8:
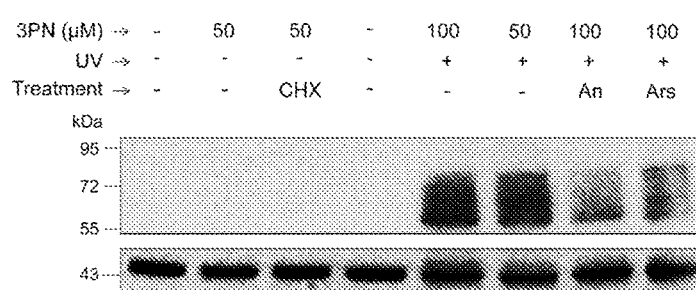
FIG. 8. 3PN and 3PO labelling activity. (a) Immunoblotting of puromycin (top) and actin (bottom) on a nitrocellulose membrane containing the cytoplasmic protein extract of MCF7 cell treated with 3PN in different conditions chx: cycloheximide, Ani: Anisomycin ars: arsenite. b) Immunoblotting of puromycin on a nitrocellulose membrane containing the total protein extract after urea lysis of cells treated with 3PO at the two different concentrations reported.
Figure 8:
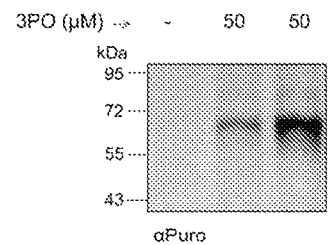

To test 3PN and 3PO activity, we treated MCF7 cells with different concentrations of the two drugs for 10 min, followed by UV-356 irradiation. Immunoblot with anti-puromycin antibody shows multiple bands with main puromycin-tag at a MW of about 65 kDa, and a less intense band at 82 kDa (FIG. 8). The immunoblot for cell pre-treated with anisomycin (An) and arsenite (Ars) revealed (FIG. 8a) a strong reduction of the labelling efficiency for both treatments as already observed for 3PB/3Bis probes.

All these results confirm a selective activity of the synthetized probes.

Protein Synthesis Activity Affects 3Px Binding

Since unmodified puromycin binds active ribosomes, we then asked if the binding of the probes is dependent on the global translation efficiency. We approach this question taking advantage of cell treatments known to elicit repression of global protein synthesis (i.e. arsenite and reduced serum concentration). We treated MCF7 cells with arsenite (1 mM, 1 hour) or we incubated the cells with 0.5% fetal bovine serum (18 hrs). Remarkably, the protein labelling efficiency is strongly reduced by both treatments (FIG. 5b), suggesting three possible causes: (i) a decrease in the target total protein abundance after stress induction, (ii) a redistribution of the target in a different cell compartment or (iii) a different affinity of the probes for the target upon stress. Additionally, monitoring the 3PB signal before and after cell treatment with low doses of cycloheximide (CHX) we did not observe detectable changes in the puromycilated protein bands intensity (FIG. 9), suggesting that short (5 min) CHX treatments at a low concentration (10 µM), do not significantly affect the labelling.

Figure 10:
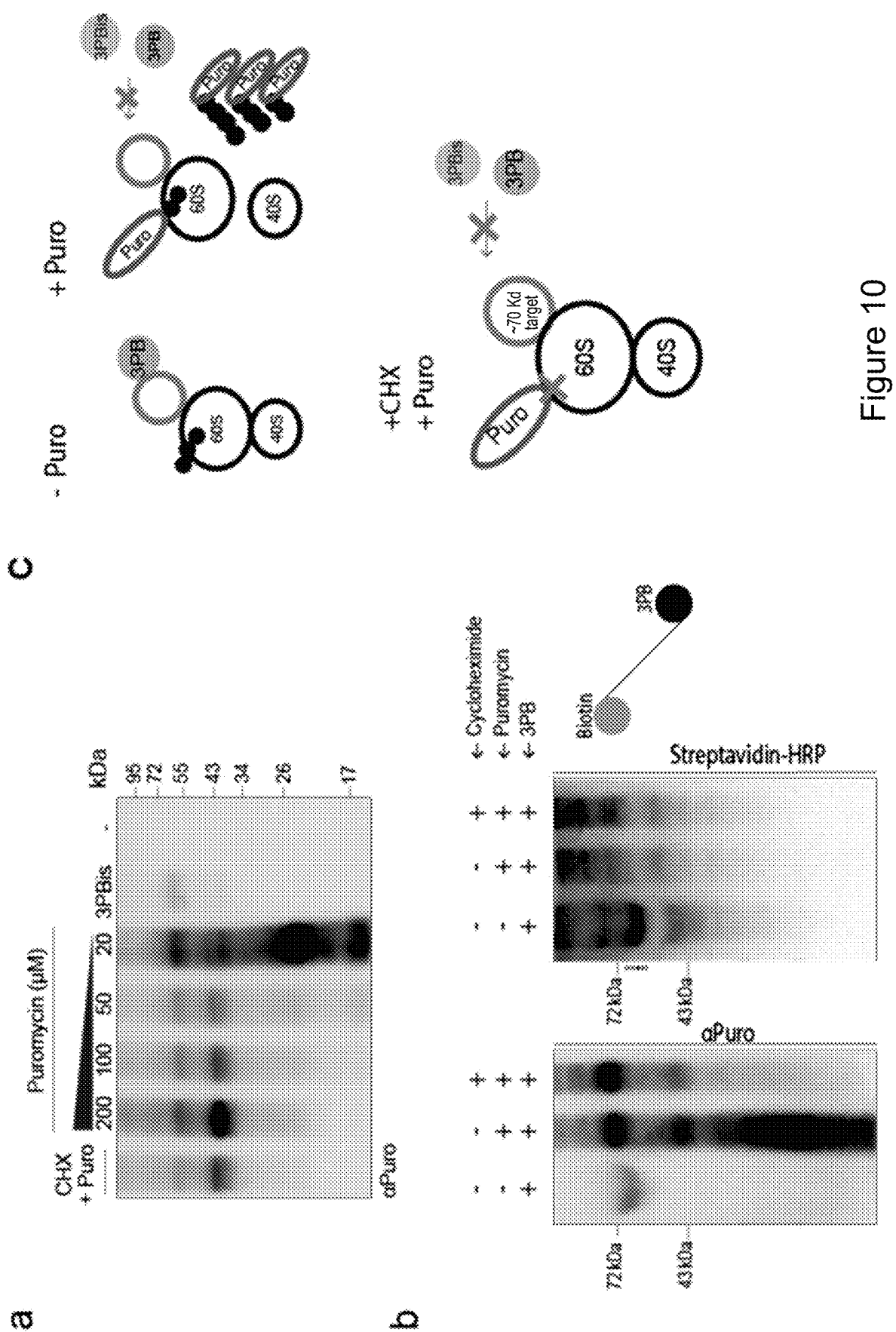
FIG. 10. Effect of ribosome inhibitors on 3PB/3PBis binding. (a) Immunoblot of puromycin on total protein extracts from, MCF7 cell treated with increasing concentrations of puromycin (incubation time: 2 hours). CHX+Puro: 350 μM CHX before puromycin treatment (20, 50, 100, 200 μM). 3PBis treatment: (50 μM, 10 min); –, not treatment. (b) On the left, immunoblot with anti-puromycin antibody on total protein extracts from MCF7 cells treat with the indicated drugs. CHX, 350 μM, 5 min; Puromycin, 100 μM, 2 hours; 3PB, 50 μM, 10 min. On the right, CuAAC coupling with Biotin-azide was performed on the cell lysate before total protein extract and SDS-PAGE. The staining of the membrane was performed with Streptavidin-HRP. (c) Sketch that summarize the effect of puromycin treatment on the 3PB-3PBis labelling.

Next, we asked if the labelling is sensitive on puromycin treatment (i.e. dependent on ribosome activity). To do that, we first treated MCF7 cell with puromycin followed by 10 min incubation with 3PB or 3PBis. When used in minimal amounts, puromycin can be incorporated in neosynthesized proteins[25], while high concentrations as well as long incubation times, fully block translation. We first define the concentration that allows puromycin to be incorporated in the nascent peptide chain (i.e. 20 µM), and the range of concentrations that completely depress translation in our biological model (i.e. 50 µM, 100 µM and 200 µM, FIG. 10a). We treat MCF7 cells with both 20 and 100 µM puromycin for 2 hours before adding 3PB (100 µM, 10 min) or 3PBis (50 µM, 10 min). Probe-labeled proteins were coupled to a Cy3-azide reporter tag using CuAAC chemistry, separated by SDS-PAGE and detected by in-gel fluorescence scanning. We observed about 50% reduction of the labelling at 65 kDa after puromycin treatment for both probes (FIG. 5c-d). Notably, 3PB binding is inhibited by a short incubation time (5 min) and low doses (20 µM) of puromycin as well (FIG. 10a). To better understand if the labelling is related to the activity of the ribosomal peptidyl transferase centre (PTC), we pre-treated cells with high concentrations of CHX (350 µM) before adding puromycin (100 µM) to fully block the ribosome catalytic activity[8]. We checked the labelling activity (FIG. 5c-d-e) performing a "click" reaction in the cell lysate, followed by SDS-PAGE and in-gel fluorescent detection. We observed a reduced labelling activity for 3PB in the CHX treated sample, while with 3PBis we obtained similar results as when we used puromycin alone. We confirmed these result by coupling the 3PB reacted probes to a biotin-azide reporter tag. After SDS-PAGE and membrane staining with streptavidin conjugated to horseradish peroxidase we observed specular affects (FIG. 10b). These results (i) confirm that puromycin alters the 3PB/3PBis protein binding with a mechanism that is mainly independent from the well-known reaction inside the ribosomal catalytic center, (ii) suggest different affinity of the probe for its target upon translational impairment (i.e. ribosome catalytic activity) and (iii) show that CHX at high concentration can hamper 3PB/3PBis binding.

Effect of the 3Px Probes on Protein Synthesis and Cell Proliferation

Figure 11:
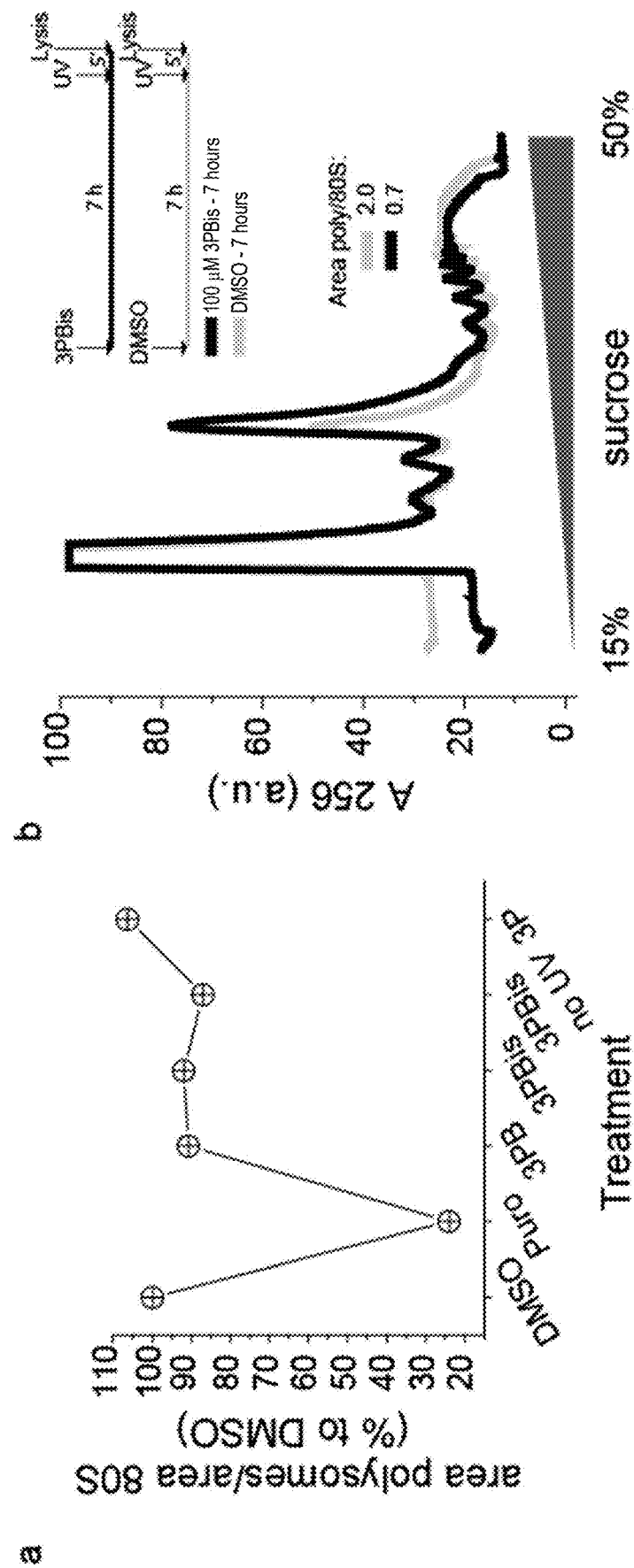
FIG. 11. Effect of the treatment on the polysome profile. (a) Values of the polysome/80S ratio calculated by comparing the area under the 80S peak and the combined area under the polysome peaks for each condition reported (10 min treatment) (b) Polysome profiles of MCF7 cells grown in a 10 nm petri dish where treated with 3Pbis or DMSO as reported. After UV irradiation of the cells, 300 μL of the cell lysate was loaded on a discontinuous 15%-30% sucrose gradient for differential centrifugation and fractionation. Values of the polysome/80S ratio are reported.

To better understand the effect of 3Px on the global translation efficiency, we compared the polysome profiles from DMSO and probes-treated cells. By treating MCF7 cells with 50 µM 3PBis or 3PB for 10 min, we observed a 10% reduction of the polysome/80S ratio (calculated by comparing the area under the 80S peak and the combined area under the polysome peaks, FIG. 11a). This effect is independent from the UV-treatment. Incubation of 3PB and 3PBis for longer times (7 hours or 18 hours) results in a depression of the polysome/80S area ratio of >50%, meaning that treatments with 3PBis can depress translation, increasing the 80S pick and reducing heavy polyribosomes (FIG. 11b). Additionally, we observed that even at high concentration polyribosomes are not depressed by the probes, suggesting an effect similar to anisomycin and cycloheximide (i.e. locking translating ribosomes on mRNA with a block of the nascent chain in the ribosome).

Identification and Analysis of 3Px Cellular Protein Targets

Figure 12:
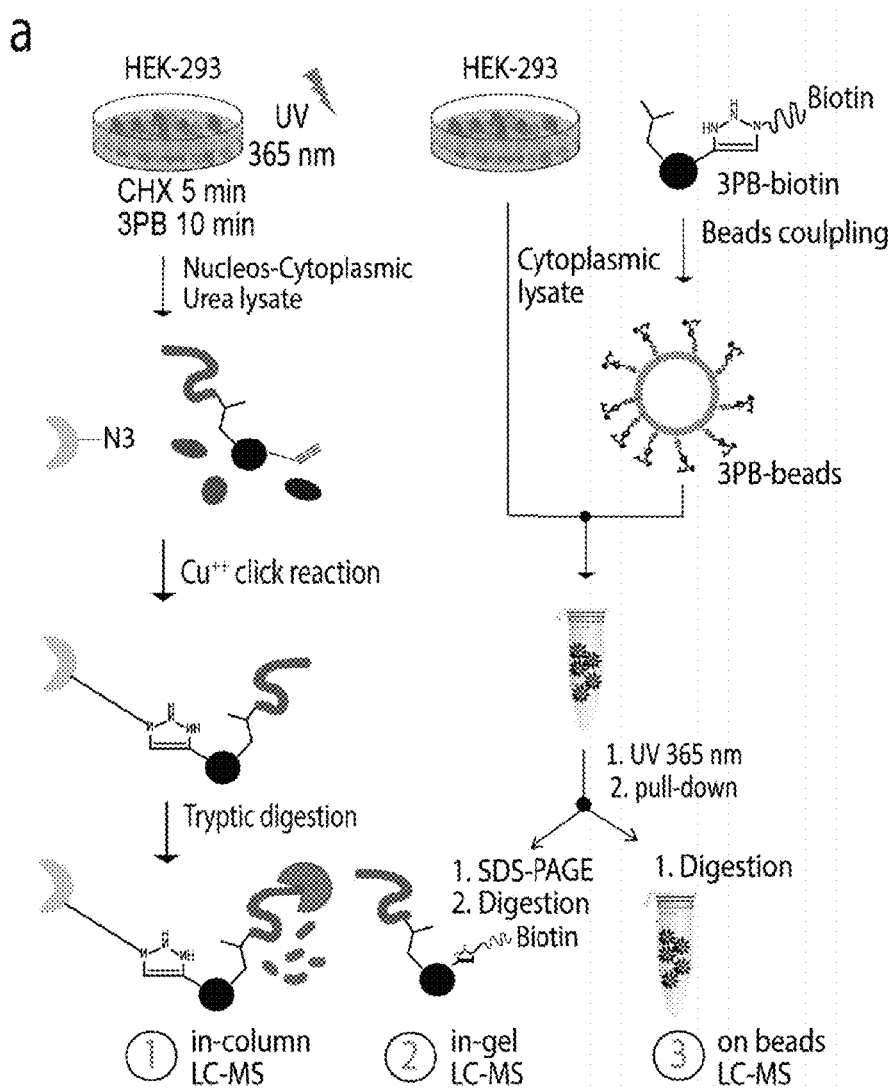
FIG. 12. Target identification (a) Overview of the experimental procedure for LC-MS/MS analysis. (b) Immunoblot with anti-puromycin antibody (left) and Ponceau staining (right) of HEK-293 cell lysates incubated with 3PB-beads. PEG-beads are used as negative control. After 1 hour incubation and washing, proteins are eluted by heating at 99° C. for 15 min in the presence of 2% SDS and samples loaded on a SDS-PAGE gel. Black arrow, unspecific bands of αPuro antibody. Black broken line, 3PB targets. (c, left) Venn diagram with the distribution of group I-III proteins, with a summary of each group's threshold and number of technical replicates across each experiment. (c, right) Fold enrichment of the top-5 proteins identified. (d) Table reporting accession number, gene name, molecular weight (MW) and PMSs peptide-spectrums match score for each of the top-5 genes. (e, left) Scheme of labelling and separation of the 3PB target by CuAAC reaction for immunoblot detection. (e, top right) Immunoblot with the indicated antibodies of total proteins purified from 3PBis-treated cells lysate after CuAAC reaction with a biotin-azide molecule followed by avidin-beads pull-down. Stars, inputs at long (right) and short (left) exposure time of the membrane during development. Black arrows, GRP78 main bands. (e, bottom) Immunoblotting of heat shock protein HSPA1/HSP70, Albumin (ALB), puromycin and GRP78 of MCF7 in normal condition or in serum starvation (0.5% FBS, 18 hours) with 3PBis (50 μM, 10 min). Black arrows: two main isoforms of GRP78 detected. (f) Immunoblot with the indicated antibodies on the total protein extract from cells treated or not treated with VER-155008 (100 μM, 1 hour) and then with 3PB (up) or 3PBis (bottom). The fold-change enrichment for a duplicate experiment is reported. (g) Co-immunoprecipitation analysis of 3PBis, GRP78, RPS6 and Hsc-70. (top) 3PBis-tagged protein was immunoprecipitated with a mouse anti-puromycin antibody. Cell lysates before immunoprecipitation (Input) and immunoprecipitates (IP) were analyzed by SDS-PAGE and immunoblotting with the indicated antibodies. R, rat anti-puromycin antibody. (bottom) Co-immunoprecipitation with Hcs-70 antibody. M, mouse anti-puromycin antibody. (h, top) Sucrose gradient absorbance profile of MCF7 cells at ~80% of confluence treated with DMSO or 3PBis. (h, bottom) 3PBis protein targets co-sediments with the translational machinery. Co-sedimentation profiles of 3PBis/αPuro, ENO1, GRP78 and RPL26 by immunoblotting. Each line corresponds to a sucrose fraction of the profile. Fractions related to the 80S pick or to the polysome region of the profile are indicated. Black arrows, GRP78 main bands. Grey arrow, RPS6. Black broken line: 3PB/3PBis labelled proteins.
Figure 12:
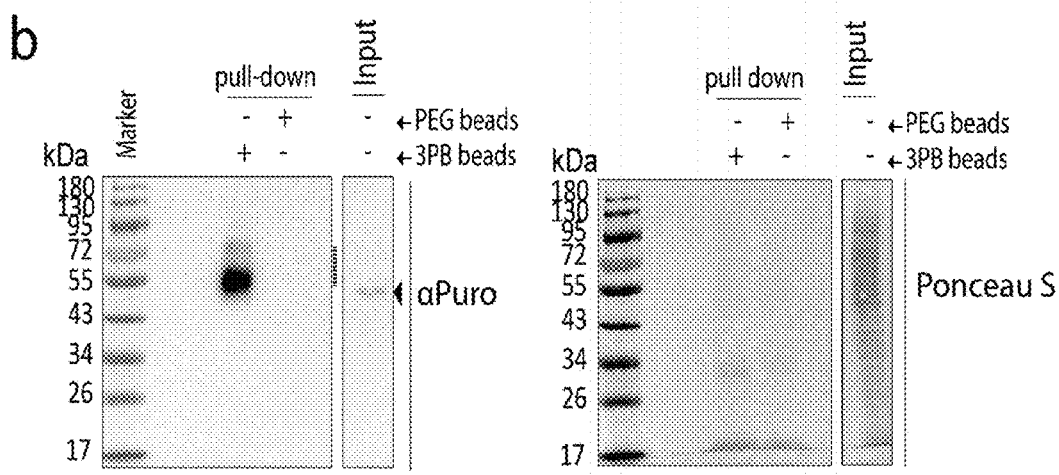
Figure 12:
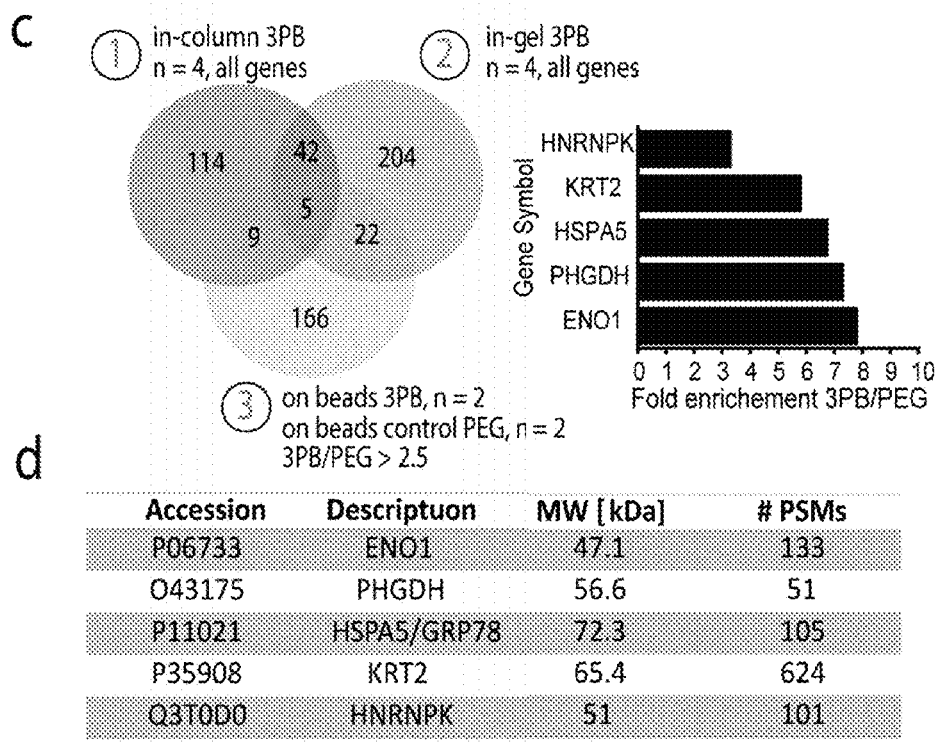
Figure 12:
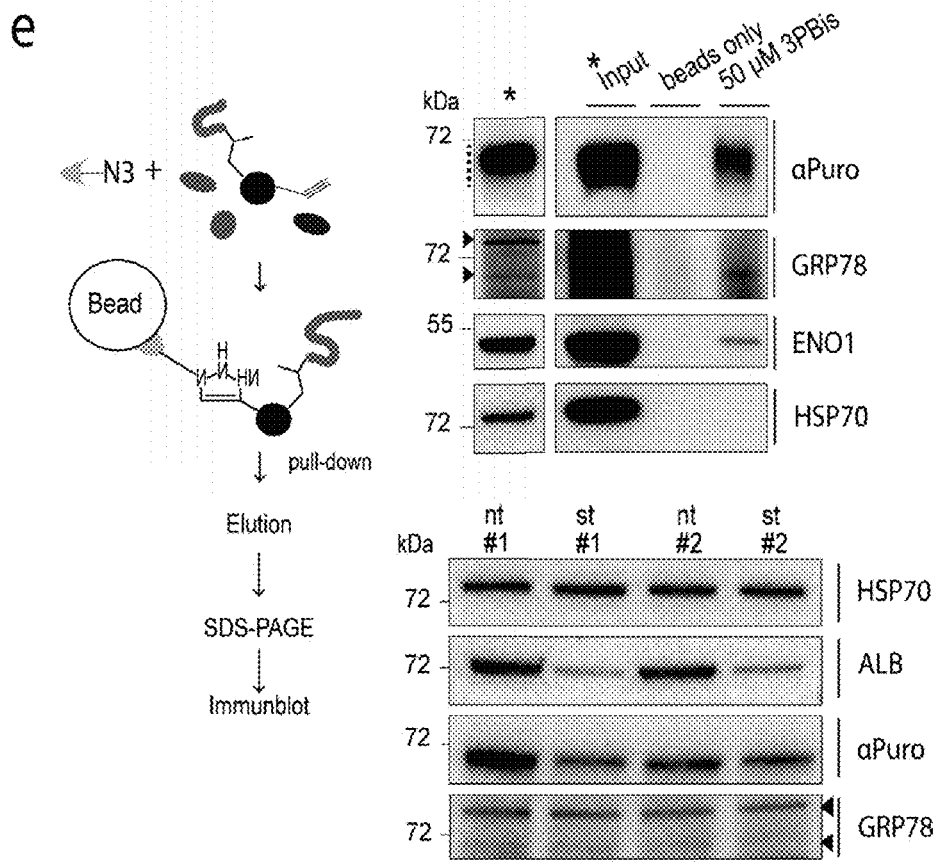
Figure 12:
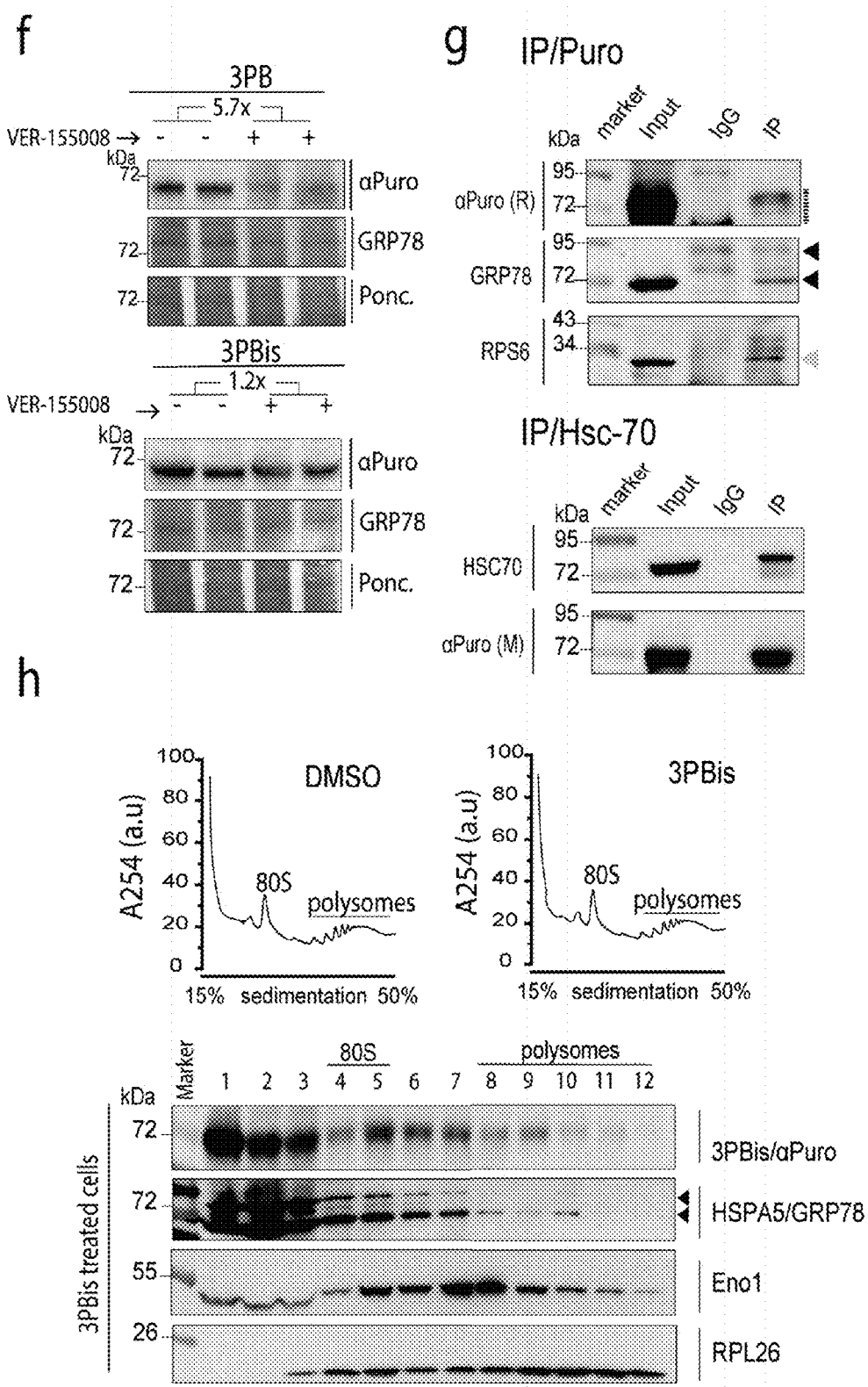

To better understand the response to inhibitory stresses and drug treatments, and to unravel the network of 3PB-binding proteins, we used two complementary approaches coupled to in-depth LC-MS studies (FIG. 12a). First, we performed an in-column digestion of target proteins after CuAAC chemistry on azide-agarose resin. Second, we pulled down the 3PB-targets with an affinity method based on 3PB-conjugated magnetic-beads, followed by in-gel and on-beads digestion of the captured proteins. Additionally, we used Peg-biotin conjugated beads to encounter for the non-specific signal.

Figure 9:
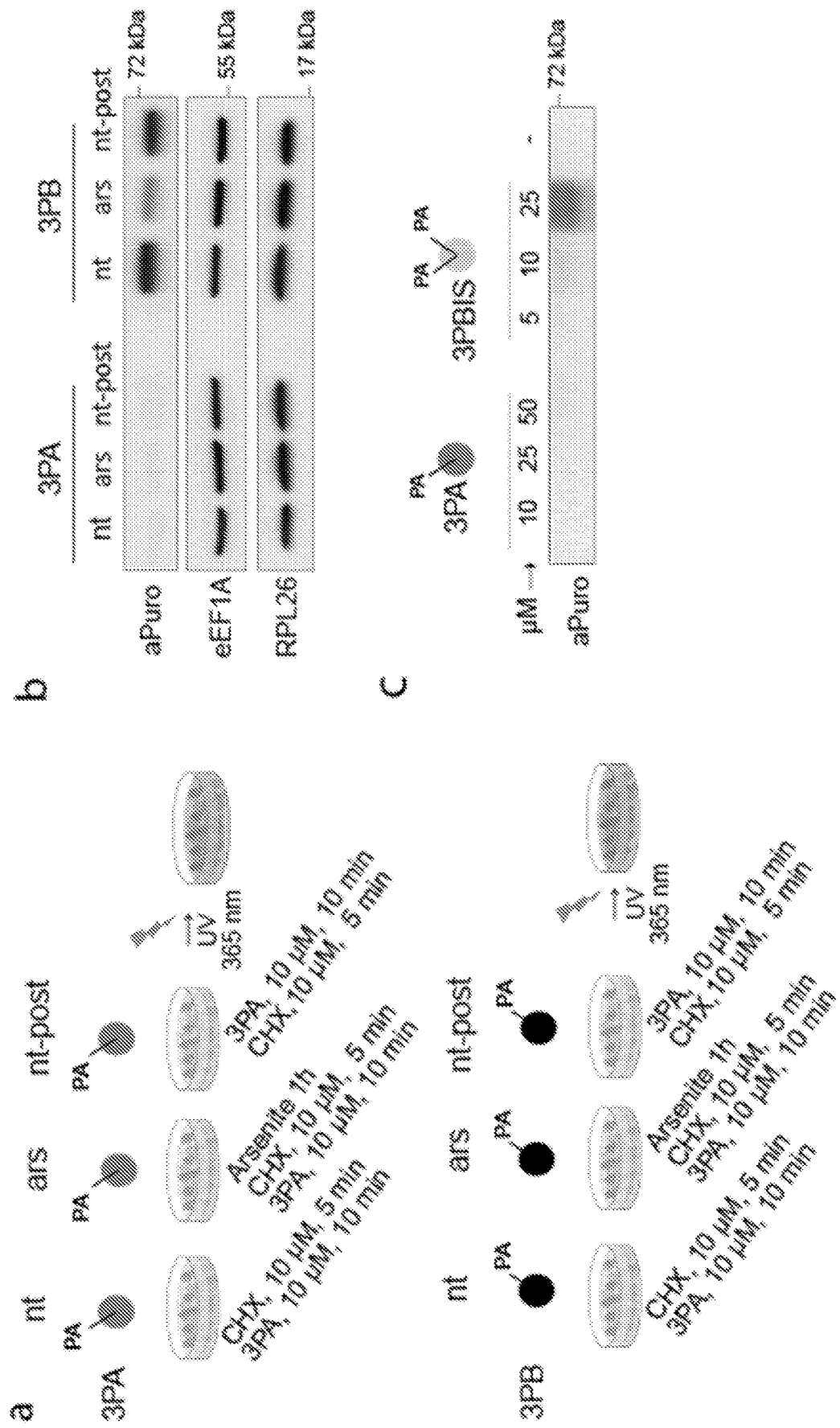
FIG. 9. Effect of short (5 min) cycloheximide treatment (10 μM). (a) MCF7 cells, treated (Ars) or not (−) with arsenite are incubated with 3PB (10 μM, 10 min) or 3PA (10 μM, 10 min) after or before (nt-post) CHX treatment (10 μM, 5 min). After UV irradiation (365 nm, 5 min, 0.75 J/cm$^2$) and lysis with hypotonic lysis buffer, proteins are quantified and loaded on a SDS-PAGE gel. (b) Immunoblotting of RPL26, eEF1α and puromycin. (c) Immunoblotting of puromycin after treating the MCF7 cells with different concentration of 3PA and 3PBIS. The position of the diazirine moiety, as well as the translation efficiency, affect the binding of the drug to the target protein. Cycloheximide (CHX) treatment (10 μg/mL) can be performed before or after adding 3PB, without affecting the binding of the new drug. PA, Diazirine photoactive moiety.
Figure 13:
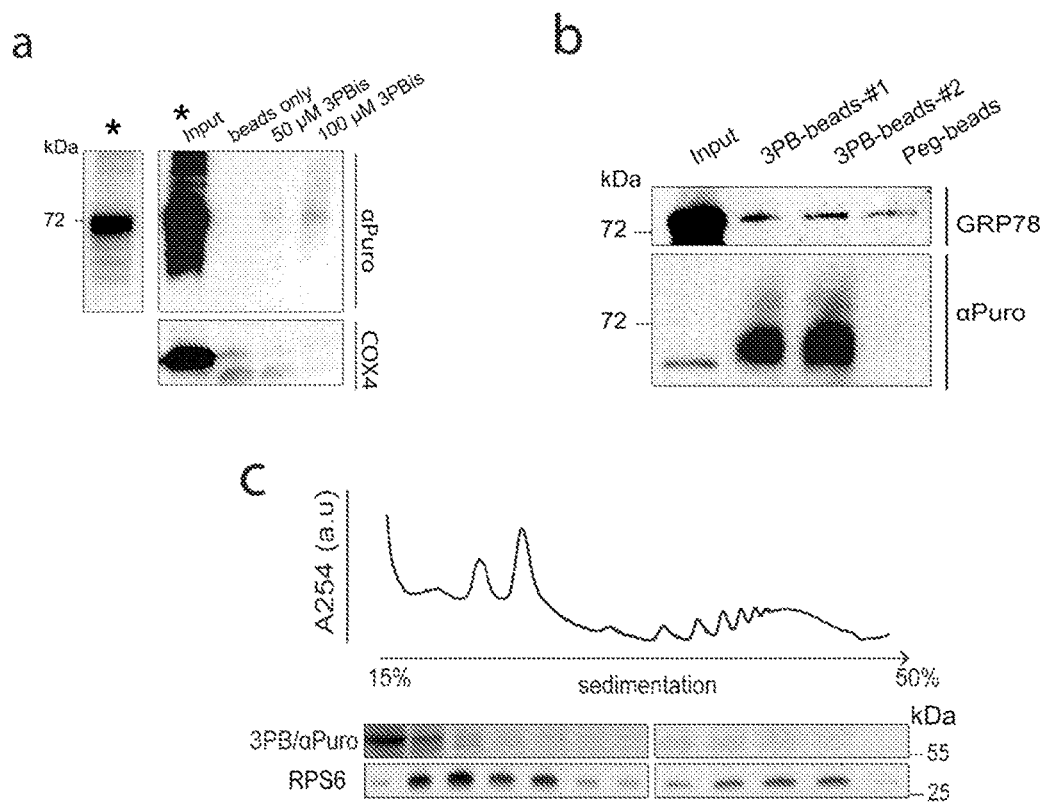
FIG. 13. 3Px labelling and pull-down (a) CuAAC reaction on MCF7 cell lysates treated with 50 μM or 100 μM of 3Pbis. After avidin-beads pull-down the detection was performed by immunoblot with the indicated antibodies. COX4 is a protein not present in our MS data and is a measure of the non-specific pull-down. (b) 3PB-beads pull-down of GRP78 protein from a MCF7 cell lysate. (c) Co-sedimentation profiles of 3PB/αPuro and RPS6 by immunoblotting.

In total, 114 protein targets were identified from in-column digestion (called data set 1, n=4), 204 targets from in-gel digestion (called data set 2, n=4) and 1085 from in-bead digestion (called data set 3, n=2, FIG. 12c). The 3PB-beads pull down reflects the "double band" pattern observed with the incubation of 3PB/3PBis in the cell lysate (FIG. 12b). To increase the stringency of our in-beads digestion data set, we performed an enrichment analysis over control Peg-beads (n=2) and we identified 333 proteins setting a cut-off fold-enrichment (FC)≥1.3 between 3PB- and Peg-beads, while 166 proteins are identified with a FC≥2.5. By using the less stringent filter (FC≥1.3) and looking for proteins in common in the three data set, we identified 15 proteins as putative 3PB targets. These factors are known to be involved in tRNAs selection and ribosome elongation (eEF1A, eEF2, eEF4G), ribosome structure (RPL18), protein folding (HSP5A, HSP90AB1, PPIA), metabolism (PHGFH, ENO1, GAPDH, ALB), RNA processing (HNRNPK) and cellular structure (KRT2, KRT10, ACTB). The use of the more stringent cut-off (FC≥2.5), allowed us to define the five candidates (ENO1, HSPA5, PHGDH, KRT2, HNRNPK) presents in all three MS data sets and at least 2.5-fold more abundant compared to control beads, suggesting that they are specific 3PB targets (FIG. 12c-d). A search of the literature revealed that ENO1, HSPA5, PHGDH, HNRNPK have been previously identified to be associated with ribosomes[12] and polysomal fractions[13] by mass-spectrometry studies, from mouse and human cells respectively. Based on the molecular weight, the number of peptide spectrum matches (PSMs) and the fold change enrichment over Peg-beads signal, we focused our attention on the heat shock protein HSPA5 (also known as 78 kDa glucose-regulated protein, GRP78), a pleiotropic chaperone protein mainly localized in the endoplasmic reticulum, involved in many functions such as nascent protein folding and unfolded protein response[26,27]. HSPA5/GRP78 undergoes post-transcriptional modifications (e.g. ADP-ribosylation and phosphorylation)[15,28] and two different isoforms are described, one of 72 kDa and a shorter splice variant of ~62 kDa (GRP78va)[19]. To validate the binding to HSP5A, we performed a CuAAC reaction in the cell lysate to conjugate a biotin-azide molecule. The anti-GRP78 antibody used recognized two main protein bands in the gel. A more abundant protein above 72 kDa, and a less intense band between 55 KDa and 72 kDa. After pull-down assay using avidin-magnetic beads (FIG. 12e and FIG. 13a) we observed the presence of the lower HSPA5/GRP78 band, while the upper band (although dominant in the input) was not detected. Additionally, we observed the presence of Eno1 (a top-5 protein hit) in the pull-down, while the immunoblot using an antibody against the ATP binding site of the parental Hsp-70 proteins did not show any signal. This result demonstrates that a HSPA5/GRP78 protein isoform is a 3PB-binder. To confirm this, we verified the presence of HSPA5/GRP78 in the 3PB-beads pull-down (FIG. 13b). Interestingly, when we incubated the beads in the cell lysate, the puromycin signal shifted above 70 kDa (FIG. 12b and FIG. 13b). GRP78 has two main protein domains, referred as (i) ATP and (ii) peptidyl binding site. Since both 3PB and 3PBis have adenosine-like moiety, we explored a possible competition on the ATP-binding site of GRP78 taking advantage of the specific inhibitor effect of VER-155008. To do that, we incubated MCF7 cells with the inhibitor for 1 hour (100 µM) before 3PB/3PBis treatment. Strikingly, 3PB labelling is reduced (5.7×), while 3PBis binding seems not affected (1.2×) (FIG. 12f). This result suggests a competitive action of 3PB with VER-155008 on the ATP-binding site of a HSPA5 isoform. Structurally related adenosine-derivate molecules are known to inhibit HSPA5/GRP78 as well as parental HSP70[29-32]. The co-immunoblot with puromycin and HSPA5/GRP78 on the same membrane, shows a common band between 55 and 72 kDa (FIG. 12e), which is consistent with the identification of a HSPA5 isoform as 3PBis/3PB target. Immunostaining with HSPA5/GRP78 and HSPA1/HSP70 does not show evident changes of the protein targets upon serum starvation (i.e. 0.5% FBS, 18 hours), suggesting that 3PB/3PBis bind only a sub-population of the HSPA5 isoform. Additionally, these last results confirm that also the 3PBis probe have preferential affinity for the targets in highly productive protein synthesis conditions (FIG. 12e and FIG. 9). Finally, since albumin was one of the top-15 protein identified by LC-MS, we tested its apparent MW by co-immunoblot, observing a ~7-10 kDa difference from the puromycin band (FIG. 12e). Therefore, we can exclude albumin main 3PB-interactor.

Interaction with Ribosomes

Figure 14:
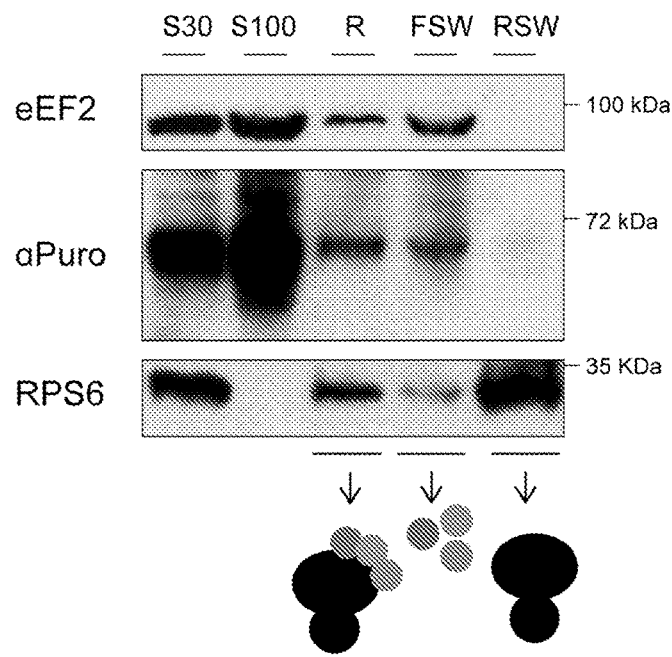
FIG. 14. Subcellular fractionation. Fractionation and immunoblot analysis of S30 (input), 5100 (soluble fraction), R (ribosomes fraction), SWR (salt washed ribosome fraction) RSW (pure ribosomes fraction) of MCF7 cells according to (Bernabò et al., 2017). The ribosomal protein S6 was used as control for ribosomal components in the fractionation. The elongation factor eEF2a was used as controls for RNA-binding protein interacting with polysomes.
Figure 15:
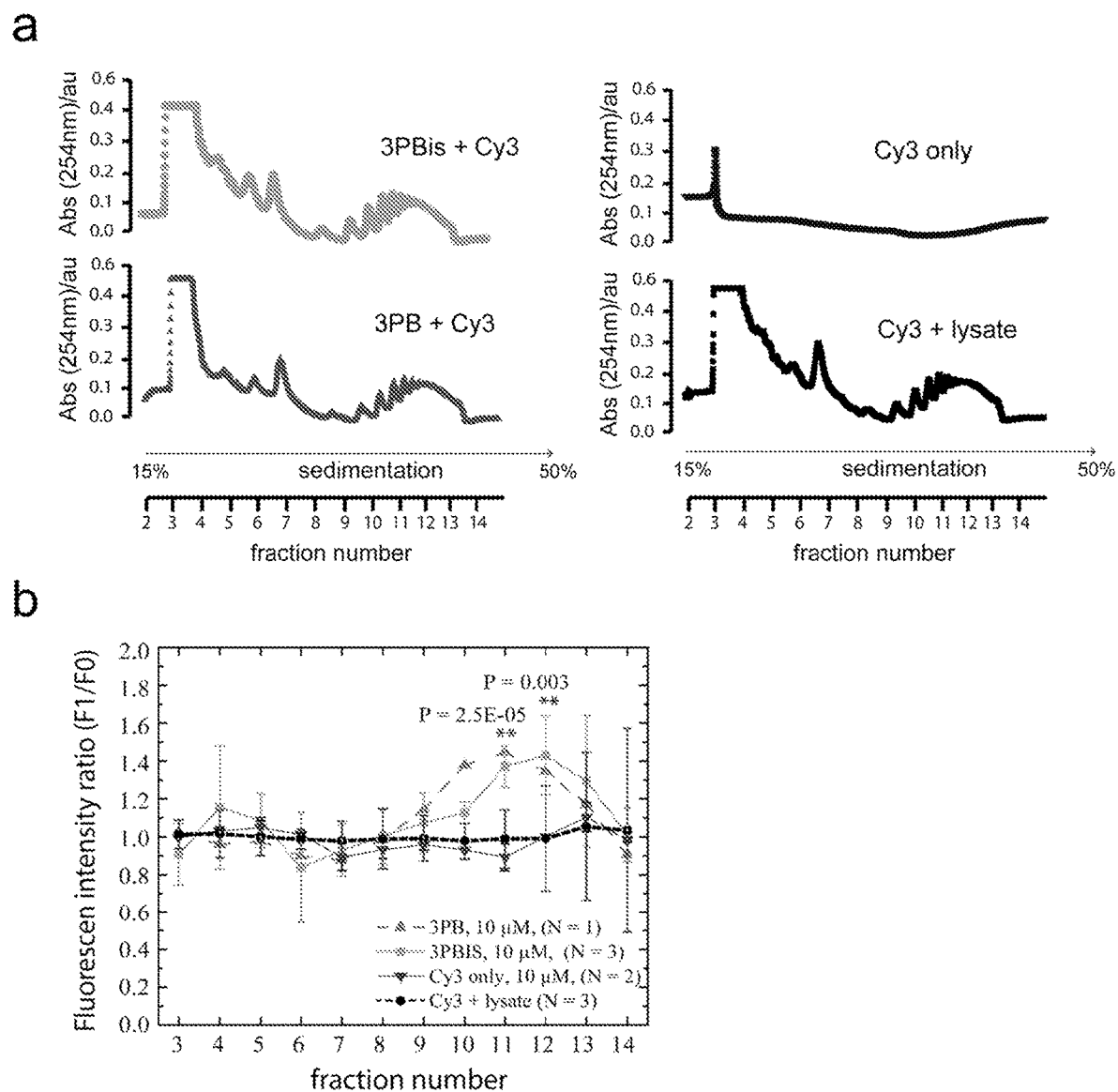
FIG. 15. Fluorescence detection of 3PB and 3PBis in the polysome profile. (a) Sucrose gradient sedimentation (15-50%) profiles of Cy3-picolyl-azide conjugated cell lysates (3PBIS+Cy3, 3PB+Cy3) and controls samples: Cy3 only and Cy3+lysate. (b) Each fraction of the profile was collected and the fluorescence of 200 μL of each fraction was measured with the spectrofluorimeter. The F1/F0 fluorescent ratio for each sample is reported. T-test P-values and number of replicates for each condition are reported in the figure.
Figure 16:
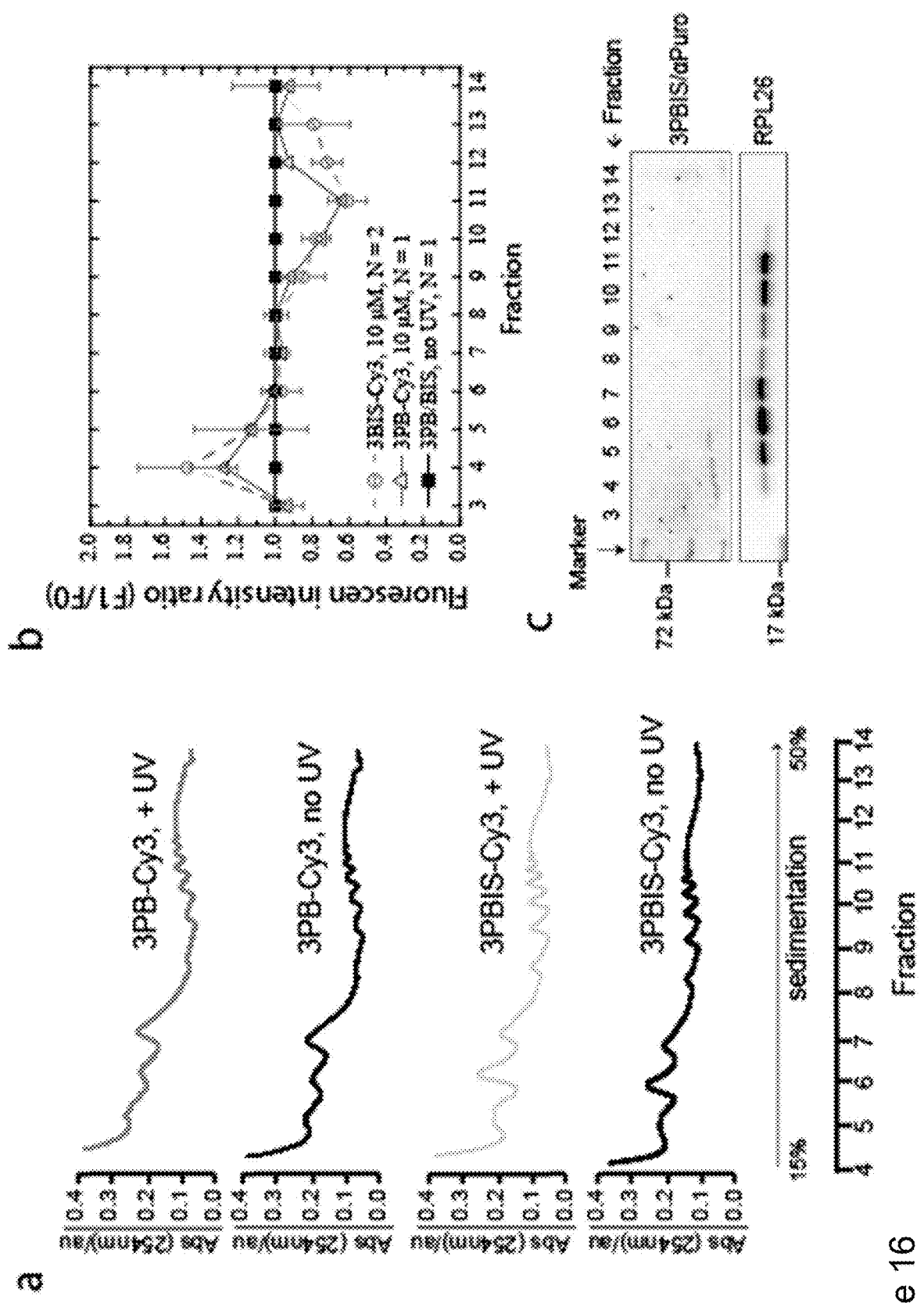
FIG. 16. 3PB and 3PBIS molecules pre-conjugated with Cy3 and reacted in the cell lysate. (a) polysome profiles of MCF7 cell lysate reacted with 3PB and 3PBIS molecules pre-conjugated molecules. (b) The F1/F0 fluorescent ratio for each sample is reported. (c) Immunoblot of puromycin and RPL26 from the protein extracted from each fraction of the 3PBis-Cy3 profile. T-test P-values and number of replicates for each condition are reported in the figure.
Figure 18:
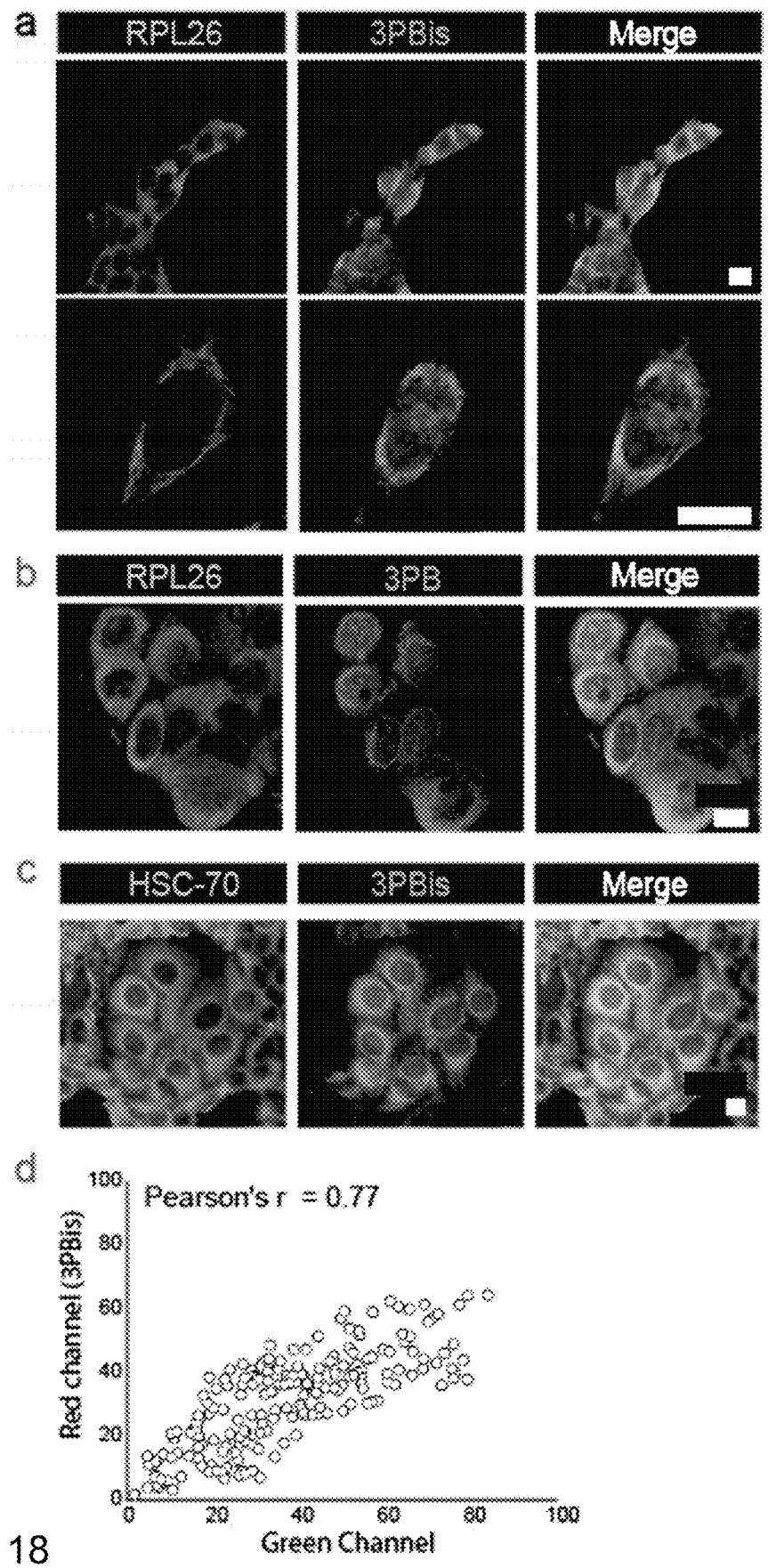
FIG. 18. 3PB and 3PBIS cellular localization observed by confocal fluorescent microscopy. Representative images of (a) 3PBIS and (b) 3PB-treated MCF7 (for RPL26) cells immunoassayed with RPL26 (up) or HSC-70 (c), and conjugated with Cy3 by Cu$^+$ catalyzed click reaction to 3Pb/3PBis labelled protein. z-stack, single plane images. FITCH Ex. Max: 492, Em. Max: 519. Cy3 Ex. Max 552, Em. Max 578. Images captured with Leica DM6000CD. Software LAS AF Version 2.7.3.9723. Scale bars, 25 μm and 10 μm and 20 μm. (d) Scatterplot of red (3PBis) and green (HSP70) pixel intensities of 3PBis-treated MCF7 cells immunoassayed with HSP70 and conjugated with Cy3 on 3PBis.

To confirm the relation of putative 65 kDa targets with ribosomes we used three complementary approaches. First, we performed a sub-cellular fractionation coupled to high-salt wash. We detect 3PBis-targets associated to the ribosome fraction (FIG. 14) as well as for the elongation factor eEF2, although a consistent fraction of the proteins is free or weakly bound, and it dissociate during centrifugation. Second, we performed a co-immunoprecipitation (co-IP) analysis with an anti-puromycin antibody, looking for the co-precipitation of ribosomal proteins. The co-IP shows the presence of the ribosomal protein S6 together with HSPA5/GRP78 (FIG. 12g), confirming the presence a structural component of the ribosome as interacting partner. The puromycin-tag proteins strongly co-immunoprecipitated with the chaperon protein Hsc-70 as well (FIG. 12g), supporting the folding of the nascent polypeptide chain during translation. Fluorescence analysis confirm the co-localization of the two proteins (Pearson's r=0.77, FIG. 18d). Third, we checked if 3PB/3Pbis labelled proteins co-sediment along the polysome profile after sucrose gradient centrifugation. The puromycin immunoblot of each fraction of the polysomal profile from 3PBis/3PB treated cells, allowed us to detect the 65 kDa probe target all along the profile (FIG. 12h and FIG. 13c). We performed a fluorescence analysis (F1/F0) after CuAAC chemistry with Cy3-azide of 3PB/3Pbis treaded cells, to confirmed the enrichment of the target proteins in the heavy polysomal fractions (FIG. 15). We detected a significant increase in the fluorescent signal in polysome (FIG. 15). On the contrary, the incubation of the cell lysate with purified pre-conjugated 3PB and 3PBis molecules with Cy3-azide, fully abrogate the labeling activity in the cell lysate (FIG. 16), implying that the binding to the targets is hampered by the structural change of the dye-conjugated probes.

Figure 19:
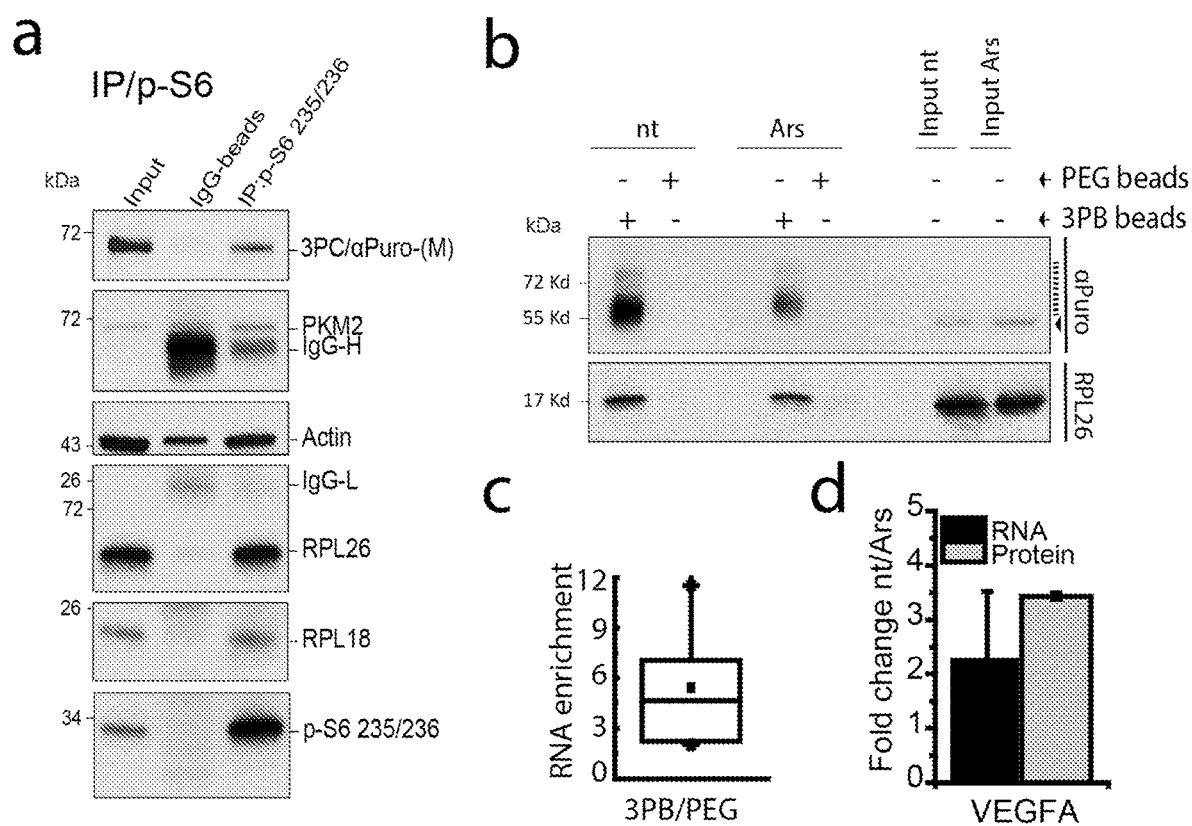
FIG. 19. Active ribosome interaction. (a) Co-immunoprecipitation analysis. 3PBis-tagged proteins were immunoprecipitated with anti pS6 (235/236) antibody. Cell lysates before immunoprecipitation (Input) and immunoprecipitated (co-IP) were separated by SDS-PAGE. The immunoblot was performed with the indicated antibodies. M, mouse anti-puromycin antibody. (b) Immunoblotting of RPL26 and puromycin on the total protein extract (inputs) and protein pull-down with 3PB-beads and control beads. HEK-293 cell lysates incubated with functionalized beads for 1 hour where washed, proteins are eluted by heating at 99° C. for 15 min in the presence of 2% SDS and samples loaded on a SDS-PAGE gel. Black broken line: 3PB targets. (c) Box-plot showing the total RNA enrichment on 3PB beads respect to control (mPEG) beads. (d) Histogram with the relative enrichment of VEGFA-mRNA on 3PB-beads (black). The total VEGFA-protein enrichment is reported on the right part of the histogram (grey).

We next asked whether our 3PBis/3PB ribosome-bound proteins mainly associate with active ribosomes. First, we took advantage of the well-known signature (p235-p236) of the phosphorylated ribosomal S6 protein (pS6), which at least in neurons is associated with translationally active cells[33]. The co-IP with pS6 shows a strong enrichment in the puromycin signal with respect to control IgG, suggesting the association with assembled and productive 80S ribosomes, while proteins not directly involved in translation (actin) do not show comparable change (FIG. 19a). This result is supported by the evidences of (i) a partial co-localization of RPL26 with Cy3-labelled 3PB/3PBis target probed by confocal microscopy (FIG. 18) and (ii) a EDTA sensitivity of the 3PBis protein targets that co-sediments with the translational machinery (FIG. 19a).

Figure 17:
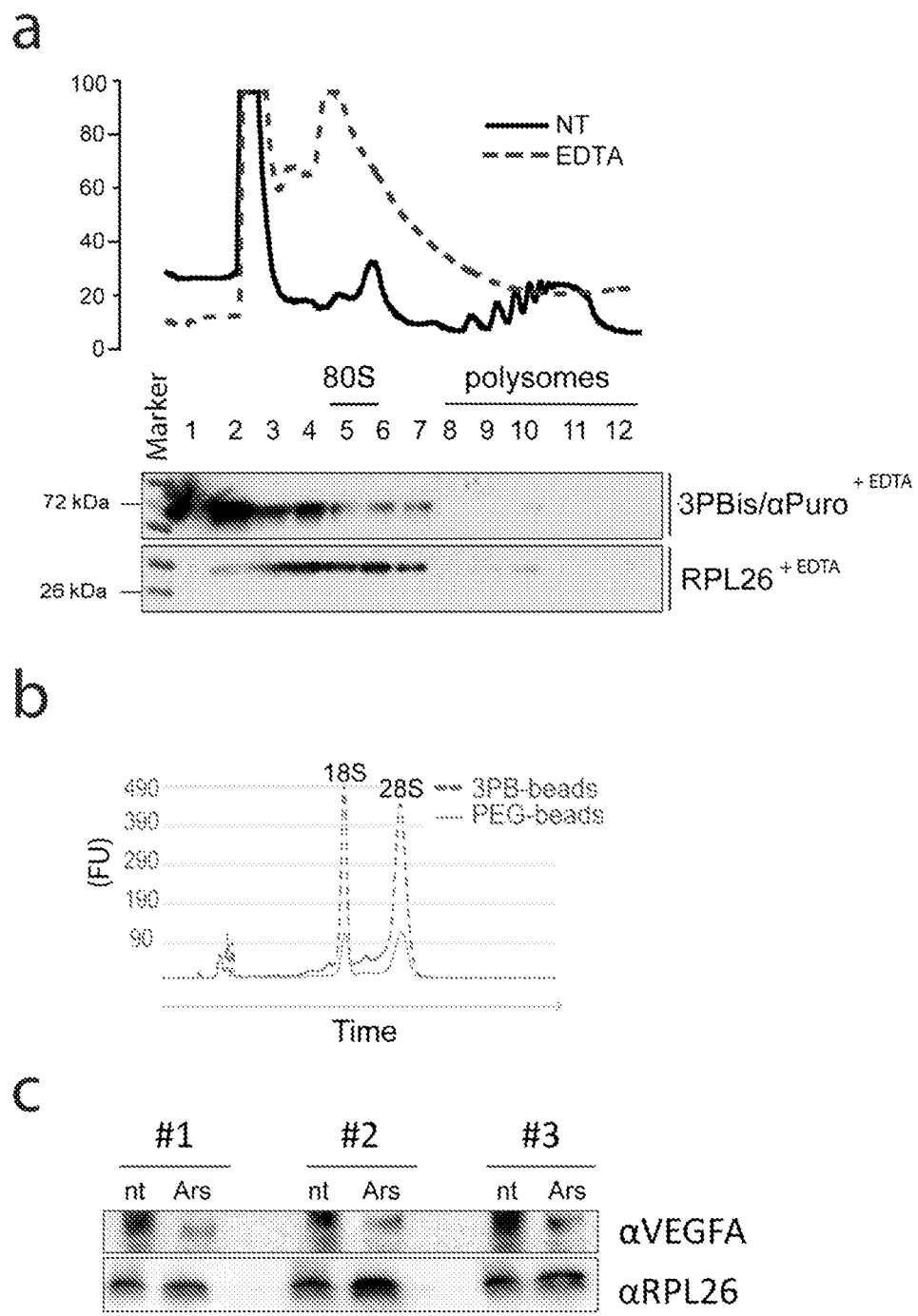
FIG. 17. Effect of 3PB and 3PBis on translating ribosome: possible applications. (a) 3PBis main protein targets are EDTA sensitive. MCF7 cell lysate was directly fractionated on a 15-50% sucrose gradient (+EDTA, black continuous line). In parallel, the other half was treated with 8 mM EDTA (+EDTA, black dashed line). Fractions were collected and analyzed by western blot with antibodies against Puromycin and the ribosomal S6 (RPS6) protein. (b) Electropherogram profile obtained with Bioanalyzer (Agilent total RNA kit, catalog no. 5067-1511) of the total RNA isolated from 3PB-beads and control beads incubated with the HEK-293 cell lysate. (c) Representative image reporting the immunoblot used for the quantification of the protein bands intensity referred to the histogram in FIG. 19d (#, independent biological replicates).

Then, we tested the possibility to capture full-length mRNA bound to ribosomes. To do that, we used 3PB-functionalyzed beads incubated with a cell lysate upon stress condition (arsenite) to confirm the preferential co-binding of puro-targets and RPL26 when translation is not depressed by arsenite treatment (1 mM, 1 h; FIG. 19b). Quantitative analysis on the total RNA pulled down with 3PB-beads shows a 3-5 fold enrichment over PEG-beads and the presence of both 18S and 28S rRNAs, suggesting the capture the full ribosome complex (FIG. 17b and FIG. 19c). Next, we purified the total RNA from 3PB-beads and we measured the relative abundance of the VEGF mRNA, in both low and high performant conditions by qRT-PCR. We observed a 2-fold enrichment of the transcript on 3PB-functionalized beads in conditions of active translation, with respect to samples treated with arsenite. This variation was specular to the total VEGF protein level (FIG. 17c and FIG. 19d). This result suggests the possibility to capture full-length mRNAs and confirm the separation of active ribosomal components.

Interaction with rRNA.

Figure 20:
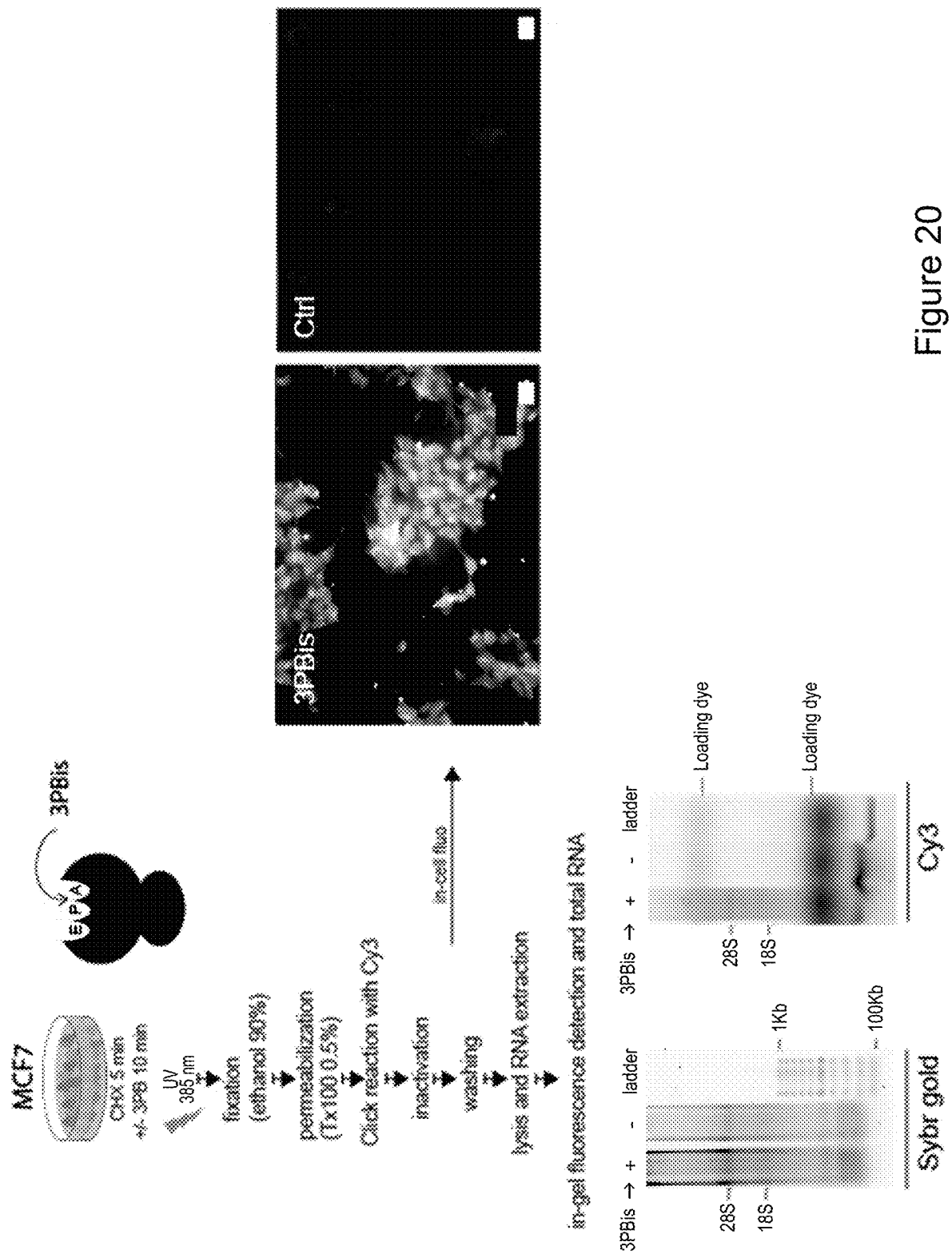
FIG. 20. 3PBis-ribosome interaction and labelling of 28S rRNA. MCF7 cells were incubated with 3PBis, fixed and conjugated with Cy3. After extraction, total RNA was run in agarose gel and stained with Syber gold or visualized by in-gel fluorescence scanning.

We investigated the possibility that 3Px molecules directly reacts in the ribosome itself. If 3Px enters the ribosome as puromycin does, it should bind only the large ribosomal subunit, and in particular the rRNA 28S that form the catalytic pocket of the ribosome. Our analysis with 3PBis confirmed the hypothesis that a fraction of the probe can directly interact with the 28S ribosomal RNA (FIG. 20), probably contributing to the stalling of ribosomes observed at higher concentration of probe and reported in FIG. 11b.

Materials and Methods

Chemical Synthesis 3PA, 3PB and 3PBis

Conversion 1+2→3 (Scheme 1)

A solution of 100 mL (d 1.015 g/mL) of BOC anhydride (100.86 gr di-tert-butyl-dicarbonate 2) in CHCl$_3$ was added in 2 h to a solution of the diethanamine 1 (7.5 gr) in CHCl$_3$ (343 ml) maintaining a temperature in the range of 0-5° C.; the final solution (443 mL) was allowed to warm to 15-18° C. and kept overnight at the same temperature. The crude reaction was then washed with a saturated solution of NaHCO$_3$ (2×300 mL) and with saturated brine (2×300 mL), the organic phase dried on MgSO$_4$, evaporated in vacuo at 40° C. to provide 6.9 g of pure mono-NBOC derivative 3 was thus obtained (80.6% yield).

NMR of 3 (CDCl$_3$): 5.21 (brs, —NHCO, 1H), 3.62 (s, —OCH$_2$CH$_2$O—, 4H), 3.55 (brt, 5.2 Hz, —OCH$_2$CH$_2$NHCO, 2H), 3.52 (t, 5.1 Hz, —OCH$_2$CH$_2$NH$_2$, 2H), 3.32 (q, 5.2 Hz, —CH$_2$—NHCO, 2H), 2.88 (t, 5.2 Hz, —CH$_2$—NH$_2$, 2H), 1.44 (s, (Me)$_3$-BOC, 9H).

Conversion 3+4→5 (Scheme 1)

To a stirred solution in acetonitrile (40 mL) of equimolar amount of amine 3 (1.938 g) and 3-(prop-2-ynyloxy)propanoic acid 4 (1.00 g), were DMAP (2 equivalent) followed by addition of EDC (1 equivalent). The resulting mixture was stirred at 19-21° C. overnight, after which it was evaporated in vacuo at 40° C., stirred in ether (50 mL) and re-acidified to pH 1 with 2M HCl (aq). Then the solution was extracted with EtOAc (50 mL), DCM (2×50 mL), EtOAc (50 mL). The organic extracts were combined, washed with sat NaHCO₃, dried (MgSO4) and evaporated in vacuum at 40° C. to provide 5 (oil, 2.00 g, yield 71.5%)

NMR of 5 (CDCl₃): δ 6.40 (brs, NHCO, 1H), 5.03 (brs, NHCO, 1H), δ 4.17 (d, 2.4 Hz, —OCH₂-alkyne, 2H), 3.81 (t, 6.0 Hz, alkyneCH₂—OCH₂—, 2H),), 3.61 (s, —OCH₂CH₂O—, 4H), 3.55 (q, 5.2 Hz, —OCH₂CH₂NHCOOBoc, 2H), 3.48 (t, 5.1 Hz, —OCH₂CH₂NHCO, 2H), 3.32 (q, 5.2 Hz, —CH₂—NHCO, 2H), 2.50 (t, 5.5 Hz, —CH₂—CONH, 2H), 2.45 (t, 2.4 Hz, alkyne-H, 1H), 1.44 (s, (Me)₃-BOC, 9H).

Alternative Conversion 3+4'→5'

To a stirred solution in acetonitrile (40 mL) of equimolar amount of amine 3 (1.938 g) and 3-Azidopropanoic acid 4' (1.00 g), were DMAP (2 equivalent) followed by addition of EDCl (1 equivalent). The resulting mixture was stirred at 19-21° C. overnight, after which it was evaporated in vacuo at 40° C., stirred in ether (50 mL) and re-acidified to pH 1 with 2M HCl (aq). Then the solution was extracted with EtOAc (50 mL), DCM (2×50 mL), EtOAc (50 mL). The organic extracts were combined, washed with sat NaHCO₃, dried (MgSO₄) and evaporated in vacuo at 40° C. to provide 5'

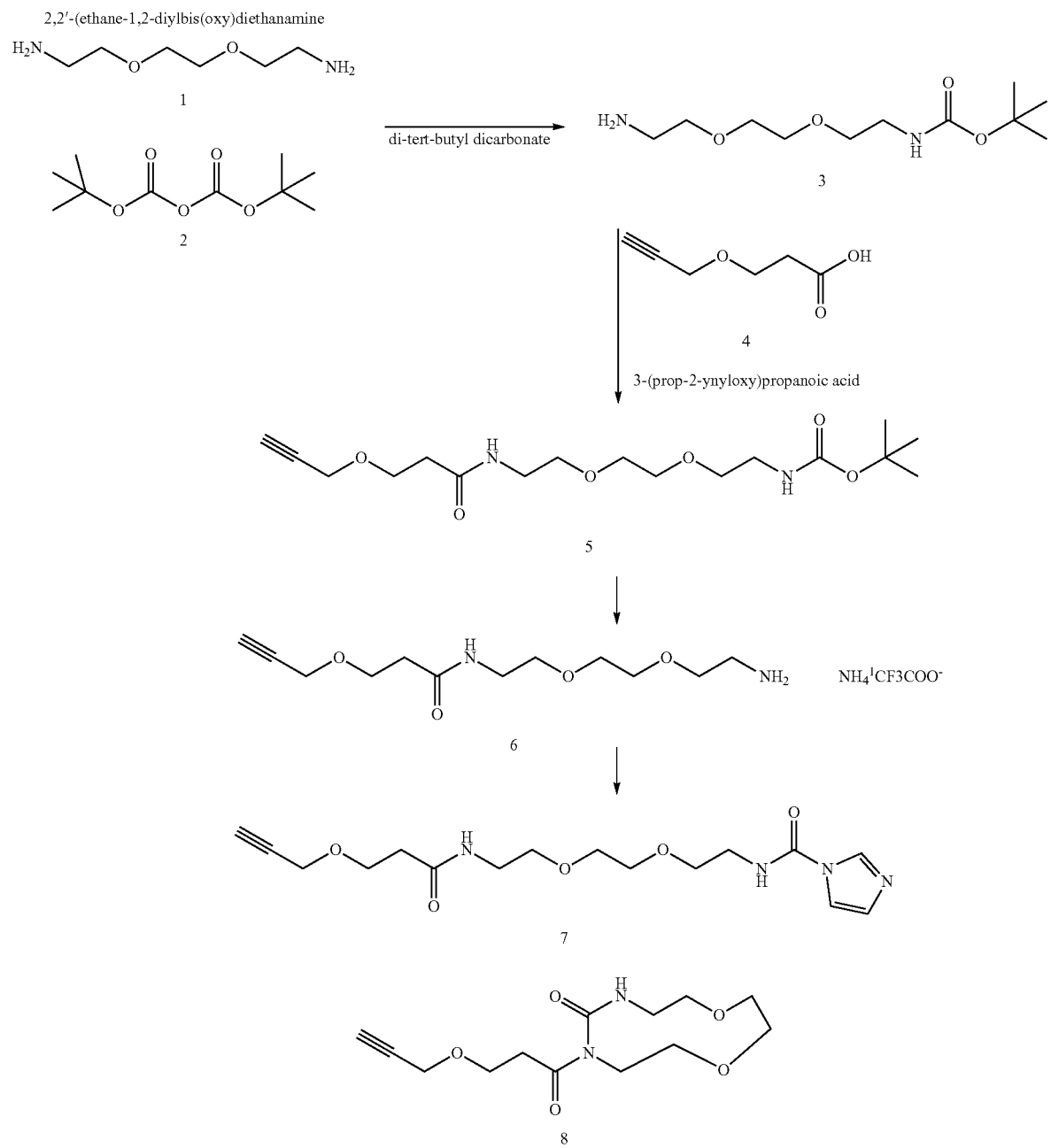

Scheme 1

21

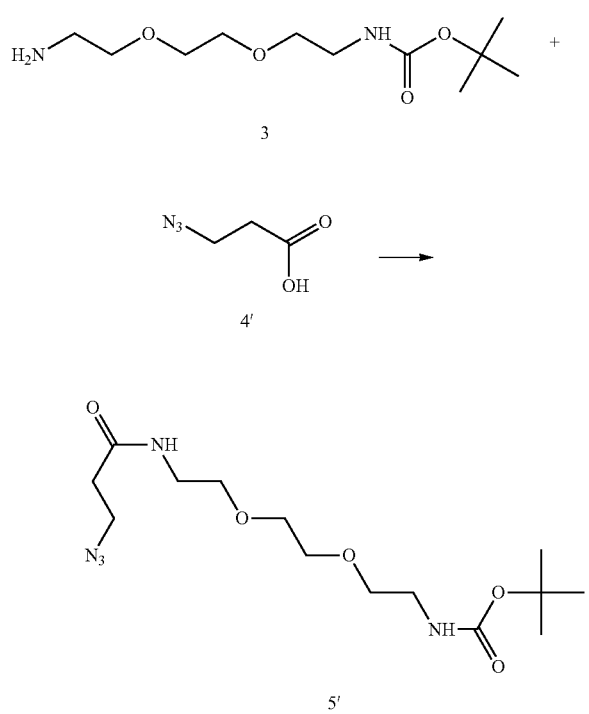

3

4'

5'

Conversion 5→6 (Scheme 1)

A stirred a solution of 5 (2 g) in dichloromethane (40 mL) was added TFA (10 molar equivalents) and kept at 20-22° C. for 3 h; after addition of 100 mL CHCl₃ the solution was evaporated in vacuo leading to a yellow oil which was further purified by stirring with K₂CO₃ (aq) (10 g/10 ml) and EtOAc (20 ml) and finally extracted. Combined organic phases were dried (MgSO₄), filtered and evaporated at 40° C. in vacuo to a viscous yellow oil. This crude material was further purified by using column Silica gel (35 g) chromatography by using dichloromethane/methanol/ammonium hydroxide gradient elution. Clean product was collected in fraction 3-7 affording a pale yellow oil still containing 1 eq of ammonium trifluoroacetate which was removed after final washing of its AcOEt solution with NH₄OH (aq) saturated with NaCl followed by extraction with EtOAc and THF.

22

Combined organic phases, dried (MgSO₄) and evaporated at 40° C. in vacuo provides 6 a clear oil (1.206 g, yield 83.7%)

NMR of 6 (DMSOd6):): δ 7.93 (brs, NHCO, 1H), 4.09 (d, 2.4, —OCH₂-alkyne, 2H), 3.62 (t, 6.1 Hz, alkyneCH₂—OCH₂—, 2H),), 3.54 (s, —OCH₂CH₂O—, 4H), 3.51 (t, 5.5 Hz, —OCH2CH2CONH, 2H), 3.42 (t, 2.4 Hz, alkyne-H, 1H), 3.40 (t, 5.1 Hz, —OCH₂CH₂NH₂, 2H), 3.20 (q, 5.2 Hz, —CH₂—NHCO, 2H), 2.87 (t, 5.2 Hz, —CH₂—NH₂, 2H), 2.33 (t, 6.4 Hz, —CH₂—CONH, 2H).

Conversion 6→7+8→10 (Scheme 1 and Scheme 2)

1.206 grams of amine 6 was treated dropwise at r.t. (22° C.) for 2 h under stirring with an equimolar amount of CDI (0.757 g) in pyridine (15 mL) under N₂ and kept under stirring at r.t. overnight.

LCMS of the crude reaction showed, besides the expected product 7, also formation of the product 8 due to internal cyclization of 7 itself. Puromycin was then added at different times (overall added amount 2.546 g) keeping the bath at 100° C. for 7 h and left overnight a with stirring at r.t. The crude was evaporated in vacuo at 50° C. affording a brown oil which was extracted by using different mixture of AcOEt/water and DCM/water partitioning system. The organic phase was purified by silica gel column chromatography (43 g) by using DCM/MeOH gradient elution obtaining at the end fractions containing almost pure 10 (LCMS>98%)

NMR of 10 (CDCl₃): δ=8.19 (s, Pur, 1H), 7.89 (s, Pur., 1H), 7.15 (d, 8.6 Hz, Pur., 2H), 7.02 (brd, 6.3 Hz, COCHNHCO, 1H), 6.83 (d, 8.6 Hz, Pur., 2H), 6.74 (brs, COCHNHCO, 1H), 6.12 (d, 7.7 Hz, PurCH-ribose, 1H), 5.73 (brs, NHCO, 1H), 5.60 (d, 4.5, 1H) 4.82 (t, J=5.8 Hz, 1H), 4.58-4.47 (m, 2H), 4.14 (d, J=2.4 Hz, 2H), 4.05 (t, J=2.4 Hz, 1H), 3.90 (d, J=12.7 Hz, 1H), 3.77 (t, J=5.8 Hz, 2H), 3.76 (s, 3H), 3.68 (d, J=11.0 Hz, 1H), 3.55 (d, J=3.7 Hz, 8H), 3.49 (q, J=5.9 Hz, 3H), 3.45-3.32 (m, 2H), 3.26 (dt, J=14.4, 7.1 Hz, 1H), 2.820 (dd, 5.9, 13.8 Hz, Ar—CH₂-purom, 1H), 2.687 (dd, 8.3, 13.8 Hz, Ar—CH₂-purom, 1H)

Scheme 2

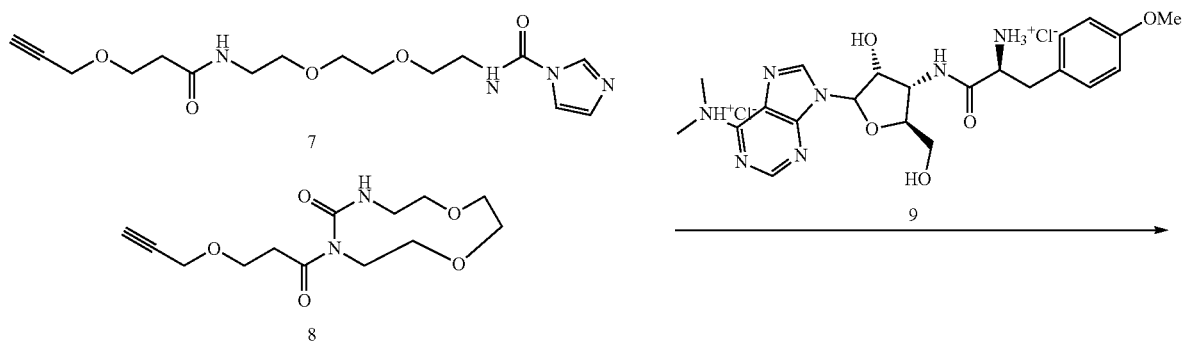

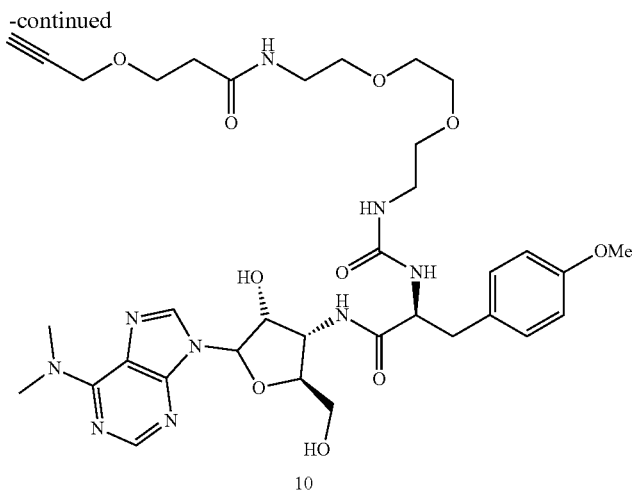

10

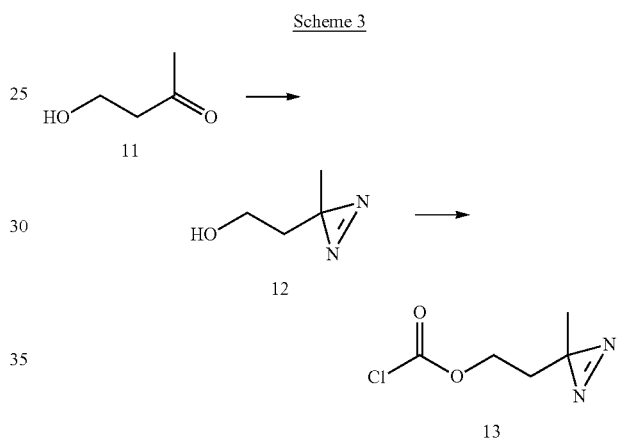

Scheme 3

Conversion 11→12 (Scheme 3)

4-hydroxy-2-butanone 11 (20 g) was stirred for 5 h in liquid ammonia at −76-71 C ° under N2; 240 mL of a methanol solution of hydroxylamine O-sulfonic acid (28 gr, 1.1 mol equivalent)) in MeOH (200 ml) was then slowly added allowing the temperature to increase at 10-15° C. and kept under stirring for 4 days. The white precipitate was filtered off, washed with MeOH (2×20 mL), the volume of the solution was carefully reduced to 100 mL (care-volatile product!) in vacuo at 30° C., the temperature was reduced to 3° C. and cooling kept at the same temperature during the addition in 30 minutes of 30 mL triethylamine (TEA, 1 molar equivalent). Then 28.8 gram of I2 (0.5 molar equivalent) was slowly added until persistence of colour and the solution allowed to reach r.t. and then stirred again for 2 h at 15° C. The total volume of the solution was reduced in vacuo at 30° C. with great care (in order to avoid losses of volatile product) to 100 mL; this solution was finally diluted with saturated brine (200 mL) and extracted with ethyl ether (2×200 mL), dried overnight on MgSO4, its volume reduced first at 10 mL ad r.t. and finally evaporated in vacuum (100 mbar) affording a yellow liquid which was then distilled at 60-62° C. (9 mbar) to yield a clear colourless liquid 12 (81 g, yield 34.4%).

NMR of 12 (CDCl3): δ 3.55 (q, 6.1 Hz, —CH2OH, 2H), 1.64 (t, 6.1 Hz, —CH2—CH2OH, 2H), 1.38 (brt, 6.1 Hz, —CH2—OH, 1H), 1.07 (s, Me-azir, 3H).

Conversion 12→13 (Scheme 3)

A stirred solution of triphosgene (2.843 gr, 0.333 mol equivalent) and pyridine (2.275 gr, 1 molar equivalent) in THF (10 ml) was kept at 18° C. under N2 for 30 minutes followed by 5 minutes at 25° C.; then the obtained thick suspension was cooled to 0-5° C. and added dropwise with the diazirine 12 (2.880 g, 1 molar equivalent) in 9 mL of THF. Immediately began to form a sticky unstirrable mixture, DCM (20 mL) was added in order to aid solution mobility and allow the addition of the remaining part of diazirine 12. After 1 h the suspension was rinsed with dry THF (2×1 mL) to give a thinner suspension, stirred for 30 minutes at 0-5° C., allowed to warm to r.t, filtered (GFF), evaporated in vacuo at 40° C. to yield a yellow oil 13 (4.26 g, yield 91.1%), stored in dark under N2.

NMR of 13 (CDCl3): δ 4.26 (q, 6.4 Hz, —CH2OCOCl, 2H), 1.76 (t, 6.4 Hz, —CH2—CH2OCOCl, 2H), 1.10 (s, Me-azir, 3H).

Conversion 10+13→14+15+16 (Scheme 4)

To a pyridine solution (7 mL) of puromycin derivative 10 (720 mg, 1 molar equivalent) stirred at r.t. under N2 were added dropwise in 30 minutes 0.2 mL in DCM of diazirine 13 (155 mg, 1 molar equivalent) and the solution was kept at 0-5 C; after 2 further addition of 13 (2 molar equivalent) in 2 h, the reaction was quenched by addition of 10 mL of distilled water and 10 mL of AcOEt; organic phase obtained after extraction were dried over MgSO4, evaporated in vacuo at 40 C to give a raw reaction products as an oil. The latter was then purified by Silica gel column chromatography (35 g) by using EtOAc/MeOH gradient elution collecting 120 fractions of 25 mL. By LC-MS and NMR analysis, fractions 13-30 contained almost pure the bis-aziridino derivative 16 (301 mg, 3PBIS, purity 95%), fractions 57-90 the mono-aziridino derivative 15 (52 mg, 3PB, purity 96%) and finally fractions 92-113 the expected mono-aziridino derivative 14 (275 mg, 3PA, purity 97%)

NMR of 3PA (400 MHz, DMSO-d6) δ 8.28 (s, purom, 1H), 8.23 (s, purom, 1H), 8.01 (d, 7.8 Hz, NHCO, 1H), 7.90 (brt, 5.3 Hz, CH2NHCO, 1H), 7.12 (d, 8.6 Hz, purom, 2H), 6.80 (d, 8.7 Hz, purom, 2H), 6.20 (d, 8.1 Hz, COCHNHCO, 1H), 6.17 (d, J=4.8 Hz, NHCO, 1H), 6.12 (t, 5.8, NHCO, 1H), 5.99 (d, 2.1 Hz, purom, 1H), 4.58 (m, riboseCH—NHCO, 1H), 4.55 (m, riboseCH-1H), 4.44 (q, 6.1 Hz, NHCOCHNHCO, 1H), 4.21 (dd, 2.7, 12.0 Hz, -riboseCH2-OCO, 1H), 4.17 (dd, 6.5, 12.0 Hz, riboseCH2-OCO, 1H), 4.07 (d, 2.4 Hz, —OCH2-alkyne, 2H), 4.01 (m, CH-ribose, 1H), 4.00 (t, 6.2 Hz, —CH2-OCO, 2H), 3.70 (s, CH3)2-N, 6H), 3.61 (t, 6.4 Hz, alkyneCH2-OCH2-, 2H), 3.47 (s, —OCH2CH2O, 4H), 3.31 (t, 5.1 Hz, —OCH2CH2NHCO, 2H), 3.39 (t, 5.1 Hz, —OCH2CH2NHCO, 2H), 3.30 (s, OCH3 purom, 3H), 3.18 (q, 5.8 Hz, OCH2CH2NHCO, 2H), 3.08 (q, 6.0 Hz, —CH2-NHCONH, 2H), 2.84 (dd, 5.9, 13.8 Hz, Ar-CH2-purom, 1H), 2.69 (dd, 8.3, 13.8 Hz, Ar-CH2-purom, 1H), 2.31 (t, 6.4 Hz, —CH2-CONH, 2H), 1.64 (t, 6.2 Hz, —CH2-aziridine, 2H), 1.00 (s, Me-azir, 3H).

NMR of 3PA 1H NMR (400 MHz, Chloroform-d) δ 8.24 (s, 1H), 7.94 (s, 1H), 7.18-7.10 (m, 2H), 6.94 (d, J=6.8 Hz, 1H), 6.86-6.77 (m, 2H), 6.72 (s, 1H), 6.03 (d, J=7.5 Hz, 1H), 5.86 (d, J=2.3 Hz, 1H), 5.66 (s, 1H), 5.50 (t, J=5.6 Hz, 1H), 4.62 (dd, J=12.9, 6.2 Hz, 2H), 4.52-4.40 (m, 2H), 4.29 (dd, J=12.0, 5.0 Hz, 1H), 4.21-4.10 (m, 3H), 4.06 (t, J=6.6 Hz, 2H), 3.76 (d, J=7.5 Hz, 5H), 3.61-3.53 (m, 6H), 3.53-3.31 (m, 4H), 3.31-3.20 (m, 1H), 3.01 (h, J=6.9, 6.5 Hz, 2H), 2.56-2.39 (m, 3H), 1.82 (s, 2H), 1.65 (td, J=6.6, 2.7 Hz, 2H), 1.04 (s, 3H).

13C NMR (100 MHz, DMSO-d6): 171.9 (s), 169.3, 157.2, 157.1 (d, CH-purom), 153.4, 151.5, 149.1, 137.2 (d, CH-purom), 129.6 (d, CH-purom), 128.9, 118.9, 112.8 (d, CH-purom), 89.2 (d, CH-purom), 79.7 (d, CH-purom), 76.4, 72.2 (d, CH-purom), 69.3 (t) 69.1 (t), 68.5 (t) 66.8 (t, CH-purom), 65.2 (t, CH-purom), 62.5 (t), 56.7 (t), 54.4 (q), 53.9 (d, CH-purom), 50.1 (d, CH-purom), 38.5 (t), 38.0 (t), 37.5 (t), 35.2 (t), 32.4 (t), 18.7 (q).

13C NMR (DEPT, 100 MHz, Choloroform-d): 171.9 (s), 169.3, 157.2, 157.1 (d, CH-purom), 153.4, 151.5, 149.1, 137.2 (d, CH-purom), 129.6 (d, CH-purom), 128.9, 118.9, 112.8 (d, CH-purom), 89.2 (d, CH-purom), 79.7 (d, CH-purom), 76.4, 72.2 (d, CH-purom), 69.3 (t) 69.1 (t), 68.5 (t) 66.8 (t, CH-purom), 65.2 (t, CH-purom), 62.5 (t), 56.7 (t), 54.4 (q), 53.9 (d, CH-purom), 50.1 (d, CH-purom), 38.5 (t), 38.0 (t), 37.5 (t), 35.2 (t), 32.4 (t), 18.7 (q).

LC/MS Ascentis Express C18 (100×4.6 mm, 2.7 μm) Column Temp.: 25.0° C. Mobile phase: 10-100% CH3CN+TFA (0.1% v/v): aq.TFA (0.1% v/v) for 10 min with 5 min; Flow: 1.8 ml/min; Wavelength: 270 nm, retention time 4.74 minutes, purity higher than 97%

MS: m/z (ES+): 882 [M+H+], m/z (ESI−): 880 [M−H−]

NMR of 3PB (400 MHz, DMSO-d6) δ 8.48 (d, 7.8 Hz, NHCO, 1H), 8.26 (s, purom, 1H), 7.93 (s, purom, 1H), 7.93 (brt, 5.3 Hz, CH2NHCO, 1H), 7.12 (d, 8.6 Hz, purom, 2H), 6.85 (d, 8.7 Hz, purom, 2H), 6.29 (d, 4.1 Hz puromicin-H, 1H), 6.18 (d, 8.4 Hz, COCHNHCO, 1H), 6.11 (t, 5.8, NHCO, 1H), 5.99 (d, 2.1 Hz, purom, 1H), 5.55 (dd, 4.2, 6.7 Hz, riboseCH—OCO, 1H), 5.25 (t, 5.5 Hz, 1H), 4.78 (q, 7.1 Hz, riboseCH—NHCO, 1H), 4.55 (m, riboseCH-1H), 4.45 (dt, 6.1, 8.2 Hz, NHCOCHNHCO, 1H), 4.10 (d, 2.4 Hz, —OCH2-alkyne, 2H), 4.02 (m, -riboseCH2-OCO, 2H), 4.01 (m, CH-ribose, 1H), 4.00 (t, 6.2 Hz, —CH2-OCO, 2H), 3.74 (s, CH3)2-N, 6H), 3.65 (t, 6.4 Hz, alkyneCH2-OCH2-, 2H), 3.52 (s, —OCH2CH2O, 4H), 3.31 (t, 5.1 Hz, —OCH2CH2NHCO, 2H), 3.39 (t, 5.1 Hz, —OCH2CH2NHCO, 2H), 3.34 (s, OCH3 purom, 3H), 3.21 (q, 5.8 Hz, OCH2CH2NHCO, 2H), 3.11 (q, 6.0 Hz, —CH2-NHCONH, 2H), 2.85 (dd, 5.9, 13.8 Hz, Ar-CH2-purom, 1H), 2.71 (dd, 8.3, 13.8 Hz, Ar-CH2-purom, 1H), 2.37 (t, 6.4 Hz, —CH2-CONH, 2H), 1.64 (t, 6.2 Hz, —CH2-aziridine, 2H), 1.00 (s, Me-azir, 3H).

1H NMR (400 MHz, Chloroform-d) δ 8.28 (s, 1H), 7.81 (s, 1H), 7.22-7.14 (m, 2H), 6.89-6.81 (m, 3H), 6.60 (s, 1H), 6.10 (s, 1H), 5.97 (d, J=7.6 Hz, 1H), 5.89 (d, J=5.8 Hz, 1H), 5.76-5.69 (m, 1H), 5.44 (t, J=5.5 Hz, 1H), 4.85 (td, J=6.8, 4.0 Hz, 1H), 4.50 (q, J=7.4 Hz, 1H), 4.21-3.97 (m, 6H), 3.93 (d, J=12.9 Hz, 1H), 3.78 (s, 3H), 3.77 (t, J=5.8 Hz, 2H), 3.70 (s, 1H), 3.64-3.55 (m, 6H), 3.52 (t, J=4.9 Hz, 2H), 3.43 (p, J=5.8 Hz, 2H), 3.40-3.31 (m, 2H), 3.12-2.96 (m, 2H), 2.50-2.42 (m, 3H), 1.68 (td, J=6.5, 2.8 Hz, 2H), 1.04 (s, 3H).

13C NMR (100 MHz, Chloroform-d) 152.0 (d, CH-purom), 137.9 (d, CH-purom), 130.3 (d, 2CH-purom), 114.0 (d, 2CH-purom), 88.6 (d, CH-purom), 85.2 (d, CH-purom), 70.6 (d, CH-purom), 70.5 (t), 70.1 (t), 69.8 (t), 66.1 (t, CH-purom), 63.9 (t), 62.2 (t), 58.3 (t), 55.7 (q), 55.2 (d, CH-purom), 50.4 (d, CH-purom), 40.1 (t), 39.5 (t), 37.8 (t), 36.7 (t), 33.5 (t), 19.7 (q).

LC/MS C18 Eclipse (100×4.6 mm, 2.7 μm) Column Temp.: 25.0° C. Mobile phase: 10-100% CH3CN+Formic acid (0.1% v/v): aq. formic acid (0.1% v/v) for 10 min with 5 min; Flow: 1.8 ml/min; Wavelength: 270 nm, retention time 5.02 minutes, purity higher than 94%

MS: m/z (ES+): 882 [M+H+], m/z (ES−): 926 [M+HCOO]−

NMR of 3PBis (400 MHz, CDCl3) δ 8.24 (s, purom, 1H), 7.94 (s, purom, 1H), 7.14 (d, 8.6 Hz, purom, 2H), 6.94 (d, J=6.8 Hz, NHCO, 1H), 6.82 (d, 8.7 Hz, purom, 2H), 6.71 (m, NHCO, 1H), 6.03 (d, 7.5 Hz, COCHNHCO, 1H), 5.66 (brs, riboseCH—OCO, 1H), 5.50 (t, 5.8, NHCO, 1H), 4.62 (q, 7.1 Hz, riboseCH—NHCO, 1H), 4.60 (m, riboseCH-1H), 4.46 (dt, 6.1, 8.2 Hz, NHCOCHNHCO, 1H), 4.46 (dd, 12.0, 8.0 Hz, —CH2-OCO, 1H), 4.29 (dd, 12.0, 5.0 Hz, —CH2-OCO, 1H), 4.17 (m, -riboseCH2-OCO, 2H), 4.15 (d, 2.4 Hz, —OCH2-alkyne, 2H), 4.06 (m, CH-ribose, 1H), 3.78 (t, 6.2 Hz, —CH2-OCO, 2H), 3.76 (s, CH3)2-N, 6H), 3.65 (t, 6.4 Hz, alkyneCH2-OCH2-, 2H), 3.52-3.30 (series of m, 8H), 3.46 (s, OCH3 purom, 3H), 3.21 (q, 5.8 Hz, OCH2CH2NHCO, 2H), 3.01 (q, 6.0 Hz, —CH2-NHCONH, 2H), 2.45 (dd, 5.9, 13.8 Hz, Ar-CH2-purom, 1H), 2.42 (t, 6.4 Hz, —CH2-CONH, 2H), 2.35 (dd, 8.3, 13.8 Hz, Ar-CH2-purom, 1H), 1.65 (t, 6.2 Hz, —CH2-aziridine, 2H), 1.04 (s, Me-azir, 3H).

LC/MS C18 Eclipse (100×4.6 mm, 2.7 μm) Column Temp.: 25.0° C. Mobile phase: 10-100% CH3CN+Formic acid (0.1% v/v): aq.formic acid (0.1% v/v) for 10 min with 5 min; Flow: 1.8 ml/min; Wavelength: 270 nm, retention time 5.02 minutes, purity higher than 97% MS: m/z MS: m/z (ES+): 1008 [M+H+], m/z (ES−) 1052 [M+HCOO]−

Scheme 4

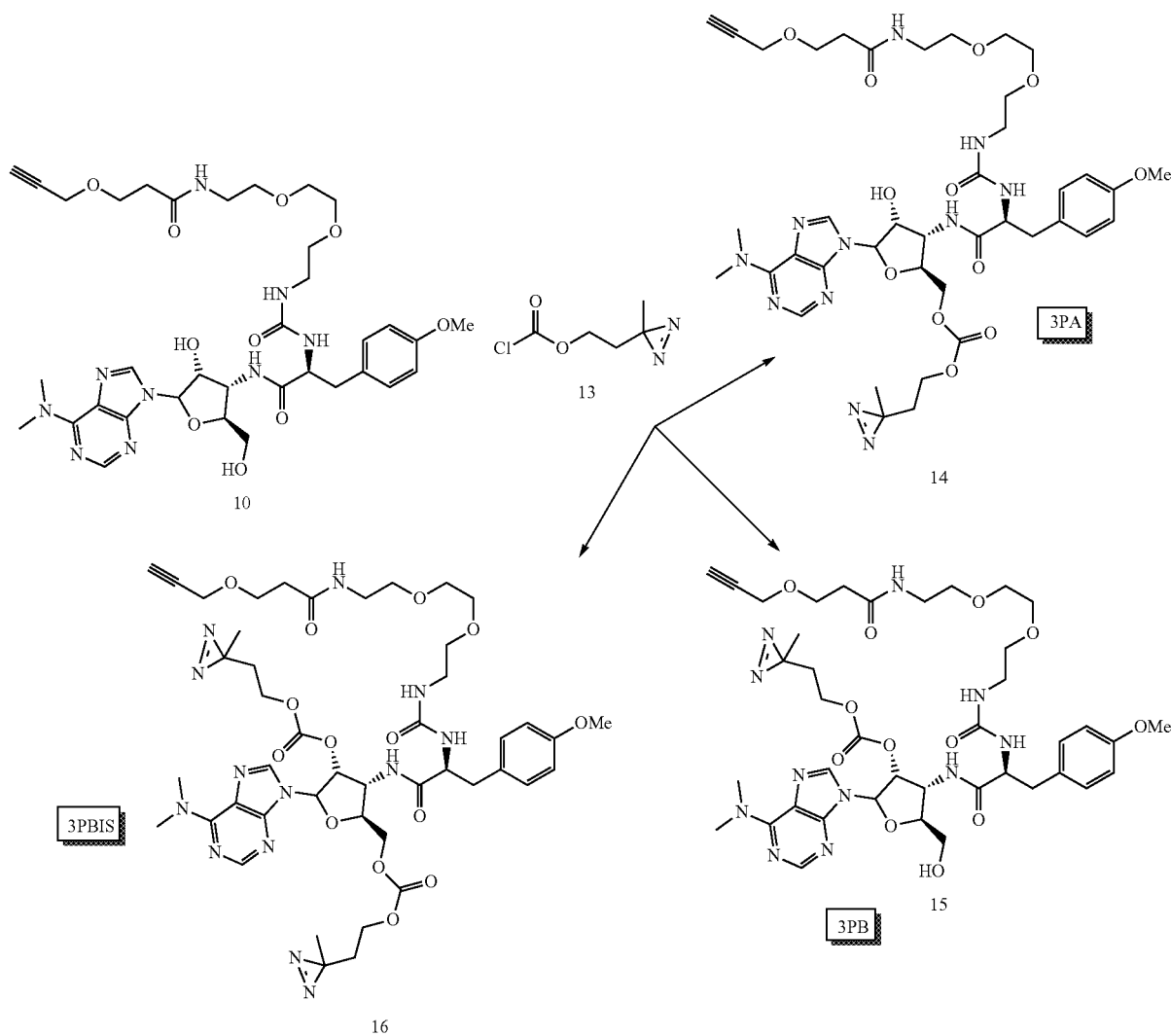

Chemical Synthesis of 3PN 8.1 mg of 2-(Prop-2-yn-1-yloxy)-4-(3(trifluoromethyl)-3H-diazirin-3-yl) benzoic acid (28.5 µmol) were dissolved in 300 µL of DMF and incubated with 64.3 mg of EDC (335 µmoL) and 31.3 mg of NHS (285 µmoL) for 3 min. This solution is called Solution A. The carboxyl group of the 2-(Prop-2-yn-1-yloxy)-4-(3-(trifluoromethyl)-3H-diazirin-3-yl) benzoic acid became susceptible to nucleophilic attack by the primary amine group of Puromycin after activation with EDC and NHS. 11.4 mg of Puromycin dihydrochloride (21 µmoL), in 300 µL PBS pH 7.4 were added under mixing to the Solution A to form the Solution B.

After that, 1.5 mL of MeOH were added and the Solution B stirring overnight. The MeOH was evaporated in vacuum to obtain a DMSO—H2O solution, called Solution C. The final product (3PN) was purified by precipitation in Na2CO3 buffer: 1 mL Na2CO3 pH 9 was added to the Solution C to form a white precipitate. This process was repeated five times. The final precipitate was dried and redispersed in 200 µL of DMSO. Total mass: 6.05 mg. Yield: 39%.

3PN-NMR data: (400 MHz, DMSO-d6) δ 8.44 (s, purom, 1H), 8.31 (m, NHCO), 8.23 (s, purom, 1H), 7.77 (d, 8.6, 1H), 7.12 (d, 8.6 Hz, purom, 2H), 7.03 (d, 8.6 Hz, 1H), 6.94 (brs, 1H), 6.83 (d, 8.7 Hz, purom, 2H), 5.99 (d, 2.1 Hz, purom, 1H), 5.04 (d, 2.4, —OCH2-alkyne, 2H), 4.58-3.98 (series of m, H's on ribose), 3.70 (s, CH3)2-N, 6H), 3.30 (s, OCH3 purom, 3H), 3.04 (dd, 5.9, 13.8 Hz, Ar-CH2-purom, 1H), 2.89 (dd, 8.3, 13.8 Hz, Ar-CH2-purom, 1H).

3PN-ESI-MS data: m/z (ESI−) m/z 736 for [M−H]− (C34H33F3N9O7-); MS/MS measurement on 736 leads to the ion fragment at m/z 708 for [M−H—N2].

Chemical Synthesis of 3PO (Scheme 5 and Scheme 6)

7.35 mg of 4-Azido-L-homoalanine HCl (1, 55 µmol) were dissolved in 300 µl of DMSO. 250 µl of NHS Diazirine (2, 50 mg/ml in DMSO, 55 µmol) and 20 µl of TEA were added. The resulting mixture was stirred at room temperature overnight. The product was extracted by with CHCl3 (1.5 ml). The organic extract was washed with 1M NaHCO3, and evaporated in vacuum to provide 3.

3 (30 µmol) was dissolved in 400 µL of DMSO was incubated with 30 mg of EDC (157 µmol) and 15 mg of NHS (136 µmol) dissolved in 400 µL PBS ph 7.4 for 1.5 h. 12.4 mg of Puromycin (23 µmol) dissolved in 1.6 ml of methanol were added drop by drop under mixing. The resulting mixture was stirred at room temperature overnight. The methanol was evaporated and the product was washed with 1M NaHCO₃, forming a white solid. The solid was collected, incubated in 1M NaHCO₃ buffer for 1 h and then recovered by centrifugation. The solid was redispersed in 200 µL of DMSO (concentration 23 mM)

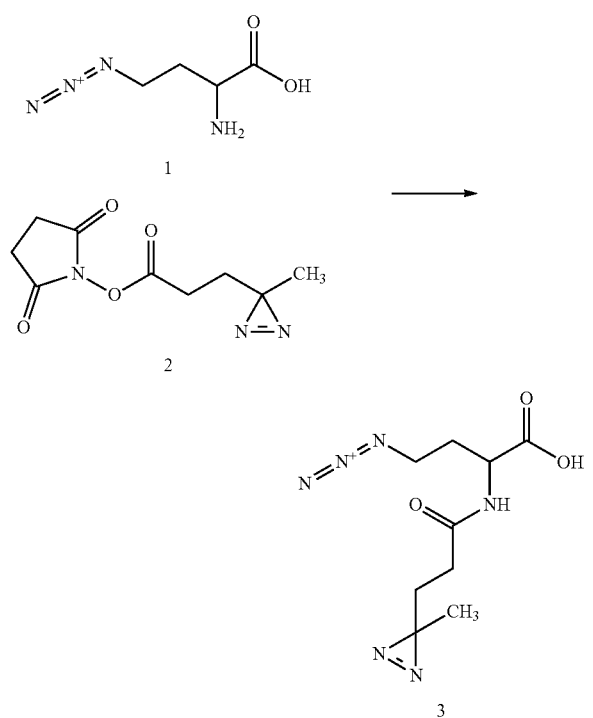

Scheme 5

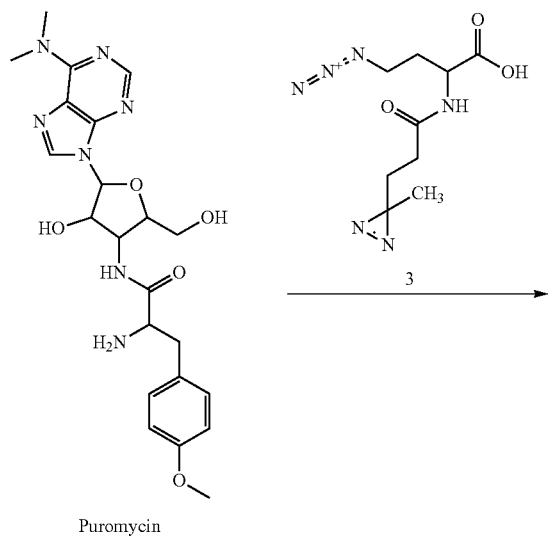

Scheme 6

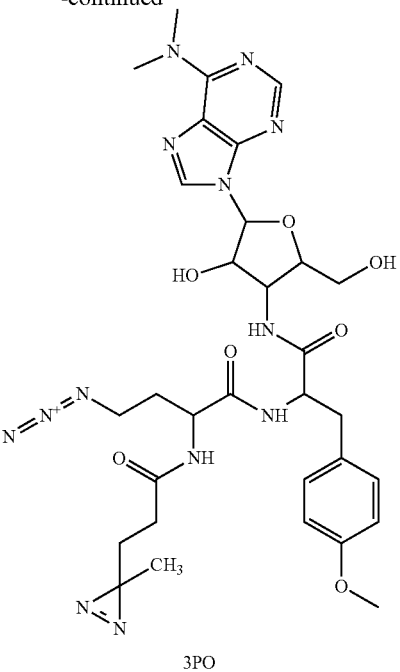

3PO

Cells and Reagents

The breast cancer cell line MCF7 (ATCC catalog no. ATCC® HTB-22™) and HEK-293 cells, were seeded on adherent plates and maintained at 37° C., 5% $CO_2$ in Dulbecco's modified Eagle's medium (DMEM) with red phenol supplemented with 10% Fetal Bovine Serum (FBS), 2 mM L-glutamine, 100 units/mL penicillin and 100 µg/mL of streptomycin. Cells were grown until 80% of confluence before lysis. Cycloheximide (CHX) was purchased from Sigma. For starvation, cells at 80% confluence were incubated with DMEM-red phenol supplemented with 0.5% FBS, 2 mM L-glutamine, 100 units/mL penicillin and 100 µg/mL of streptomycin. Cells were kept under starvation for 18 hours at 37° C., 5% $CO_2$. Arsenite treatment was performed using cells at 80% confluence, adding arsenite at a final concentration of 1 mM for 1 hour.

Detection of Reactive Oxygen Species

The UV treatment was performed on ice, wherein MCF7 were also treated with 200 µM hydrogen peroxide for 20 min at 37° C. The cells were then stained with 5 µM of CellROX Deep Green Reagent (Thermo, catalog no. #C10444) by adding the reagent to the fresh complete medium and incubating the cells at 37° C. for 30 minutes. Cells were then washed with PBS three times, fixed with ProLong Gold Antifade (Invitrogen, Catalog no P36962), pictures were collected by fluorescent microscopy (LeicaDM6000CS) and analyzed by Image J v1.51n.

Preparation of Cell lysates

MCF7 and HEK-293 were seeded at $1.5 \times 10^6$ cells per 100 mm dish and grown until they reached 80% of confluence. Cells were washed thrice with chilled PBS complemented with cycloheximide 10 µg/mL and harvested with urea lysis buffer (200 mM Tris, 4% CHAPS, 1 M NaCl, 8 M Urea, pH-8) or hypotonic cytoplasmic lysis buffer (10 mM NaCl, 10 mM $MgCl_2$, 10 mM Tris-HCl, pH 7.5, 1% Triton X-100, 1% sodium deoxycholate, 5 U/mL DNase I, 200 U/mL RNase inhibitor, and 10 µg/mL cycloheximide). After hypotonic lysis, nuclei and cellular debris were removed by two centrifugations at 18000 g, 4° C., 5 min. RNA absorbance was measured (260 nm) by Nanodrop ND-1000 UV-VIS Spectrophotometer before use or storage. The lysate was aliquoted and stored at −80° C. for not more than a month to avoid freeze/thaw cycle.

Nucleus and Cytoplasm Fractionation

Nuclear and Cytoplasmic fractions were extracted from MCF-7 after cells were treated with CHX (10 ug/ml, 5 min, 37 C) and 3PB or 3PBis treatment (10 min, 37 C) followed by irradiation under a UV lamp at 365 nm for 5 min (0.75 J/cm2). Cells were washed thrice with chilled PBS supplemented with CHX (10 ug/ml) and cytoplasmic extraction was obtained using hypotonic cytoplasmic buffer (10 mM NaCl, 10 mM $MgCl_2$, 10 mM Tris-HCl, pH 7.5, 1% Triton X-100, 1% sodium deoxycholate, 5 U/mL DNAseI, 200 U/mL RNase inhibitor, and 10 μg/mL cycloheximide) and pelleted at 23000 g, 4° C., 5 min. The supernatant collected was cytoplasmic fraction and the pellet containing nuclei were washed 10 times with PBS to remove cytoplasmic contaminants. Nuclei pellet were resuspended in urea lysis buffer (200 mM Tris, 4% CHAPS, 1 M NaCl, 8 M Urea, pH-8) followed by sonication. Samples were quantified with Bradford Protein assay and equal amount of proteins were resolved on SDS polyacrylamide gel.

Cell Treatment with 3Px Probes.

Reaction in cell culture: MCF7 or HEK-293 cells were grown to 80% of confluence and treated with CHX (10 μg/mL, 5 min, 37° C.) and then with the probe (10 min, 37 C). Cells were then washed with cold PBS (containing CHX 10 μg/mL), placed on ice and irradiated under a UV lamp (BLX-365, 5×8 W) at 365 nm for 5 min (0.75 $J/cm^2$) followed by lysis with hypotonic cytoplasmic buffer. Reaction in the cell lysate: HEK-293 or MCF7 cells were treated with CHX (10 μg/mL, 5 min). After hypotonic lysis and precipitation of nuclei and cellular debris by centrifugations at 18000 g, 4° C., 5 min, the supernatant was diluted to A260=1 a.u/μL with 10 mM NaCl, 10 mM $MgCl_2$, 20 μg/mL cycloheximide, 10 mM Hepes, pH 7 in DEPC water, to a final volume of 150 μL. The diluted lysate was then incubated with the reactive probe for 1 hour in a 12-well plate and then UV-irradiated (BLX-365) at 365 nm for 5 min (0.75 J/cm2).

Proteomic Analysis.

HEK-293 cells or cell lysates were used for LC-MS analysis. In-column digestion. Purification and digestion of the chemically-bound 3PB-target proteins was performed using the Click Chemistry Capture Kit (Jena Bioscience, cat. no. CLK-1065) according to the manufacturer's instruction. Data from four independent samples were collected. In-gel digestion of gel slices. Gel slices were digested using ProGest digestion robot overnight. Data from four independent samples were collected. On-bead digestion. Beads were denatured in a urea buffer composed of urea (6M) and thiourea (2M), and then reduced in DTT (10 mM) at 37° C. and 1200 rpm for 1 hour. Then samples were alkylated by adding IAA (final concentration 50 mM) in dark for 1 hour. The magnetic beads were washed with TEAB (100 mM) for 4× and then combined with the urea buffer. Samples were digested with 1 μg of trypsin in 100 ul of 100 mM TEAB overnight at 37° C. and 1400 rpm. The digested samples were purified using Bravo Assay MAP afterwards. Data from two independent 3PB-beads samples and two PEG-beads where collected. Magnetic beads where from IMMAGINA Biotechnology (cat. no. 016-00-007-2-1) and GE Healthcare (cat. no. 28-9857-38). LC-MS. After tryptic digestion samples were resuspended in 40 μl of 2% ACN, 0.05% TFA in HPLC $H_2O$, then 15 μL of samples were separated by reversed phase nanoflow HPLC (EASY-Spray C18, 50 cm×75 um, Thermo RSLCnano) (0-37 min, 4-30% B; 37-40 min, 30-40% B; 40-45 min, 40-99% B; 45-50 min, 99% B; 50-80 min, 4% B; A=0.1% FA in HPLC $H_2O$; B=80% ACN, 0.1% FA in HPLC $H_2O$) and directly analyzed by Q Exactive HF using (i) full ion scan mode m/z range 350-1600 with resolution 60,000 (at m/z 200), lock mass m/z=445.12003 (in-gel samples) and (ii) full ion scan mode m/z range 350-1500 with resolution 120,000 (at m/z 400), lock mass m/z=445.12003 (on-beads samples). In-gel and in-column MS/MS was performed using HCD with resolution 15,000 on the top 15 ions with dynamic exclusion. On-beads MS/MS was performed using CID on the most abundant ions with cycle time 3 seconds and with dynamic exclusion.

Pipeline Data Analysis

Raw files from gel bands were analyzed using Proteome Discoverer 2.2 (Thermo Fisher) against UniProt/SwissProt human and bovine database (2017_01, 26169 protein entries) as the cells were cultured with bovine serum, using Mascot 2.6.0. The mass tolerance was set at 10 ppm for the precursor ions and at 20 mmu for fragment ions. Carboxyamidomethylation of cysteine was used as a fixed modification and oxidation of methionine as variable modifications. Two missed cleavages were allowed. The precursor peak area was used for protein quantification. Raw files from beads were analyzed using Proteome Discoverer 2.2 (Thermo Fisher) against UniProt/SwissProt human database (2017_01, 20171 protein entries) using Mascot 2.6.0. The mass tolerance was set at 10 ppm for the precursor ions and at 0.8 Da for fragment ions. Carboxyamidomethylation of cysteine was used as a fixed modification and oxidation of methionine as variable modifications. Two missed cleavages were allowed. The precursor peak area was used for protein quantification. For in-column digestion data: all the gene having at list a signal in at least one of the four replicates were included in the analysis. For in-gel digestion data: we removed all the proteins that were not detected in the input and we kept all genes having at list a signal in one of the four replicates. For in-beads digestion data: to account for low abundant protein we set a value of 25998.91992 (minimal detected value in all samples) for all the protein not detected in 3PB-beads or PEG-beads samples. Since we used two different types of commercial beads for pull-down (Magar—Immagina Biotech cat-no 016-00-007-2-1 and Sepharose—GE healthcare cat. no 28985799), we calculate the ratio of (D1) 3PB Magar-beads/(E2) PEG magar beads and (D2) 3PB sepharose beads/(E2) PEG sepharose beads. All the proteins with a mean FC enrichment ≥1.3 or ≥2.5.

Immunoblotting

Cell lysates were prepared as described above. Proteins were separated by SDS-polyacrylamide gel electrophoresis and transferred onto PVDF membranes. Samples were heated at 95° C. for 10 min in 6× Laemmli loading buffer and run in a SDS-PAGE in 25 mM Tris, 192 mM glycine (Biorad, catalog no. 4569033) at 120 V for 50 min. Membranes were blocked in 5% milk (Santa Cruz catalog no. SC-2325) in TBS-Tween (0.1% Tween) for 1 hour, incubated in primary antibody o.n. at 4° C., then washed in TBS-Tween (0.1%, TBST) three times, 10 min each. After incubation with secondary antibodies conjugated to horseradish peroxidase, blots were washed three times in TBS-Tween (5 min each) and processed by ECL Plus detection kit as instructed by the supplier (GE Healthcare, Amersham ECL Prime catalog no. RPN2232) or SuperSignal™ West Femto Maximum Sensitivity Substrate (Thermo Scientific catalog no. 34095).

List of Antibodies Used:

| Antibody | Company Supplier | Dilution/amount (IP: immunoprecipitation WB: immunoblotting) | Catalog no. |
|---|---|---|---|
| Mouse monoclonal anti calnexin | EMD Millipore | IP - 6 µg<br>WB - 1:3000 | MAB3126 |
| Mouse monoclonal anti Puromycin | EMD Millipore | IP - 6 µg<br>WB - 1:5000 | MAB3126 |
| Rat monoclonal anti Puromycin | EMD Millipore | WB - 1:5000 | MABE341 |
| Rabbit monoclonal anti GRP78 | Abcam | WB - 1:1000 | ab108613 |
| Sheep polyclonal anti Serum Albumin | Abcam | WB - 1:1000 | ab8940 |
| Rabbit polyclonal anti RPL18 | Abcam | WB - 1:1000 | ab207555 |
| Rabbit IgG | Pierce - Thermo Scientific | IP - 6 µg<br>WB - 1:1000 | 31235 |
| Mouse IgG | Pierce - Thermo Scientific | IP - 6 µg<br>WB - 1:1000 | 31903 |
| Mouse monoclonal anti HSP90 | Abcam | WB - 1:2000 | ab13492 |
| Rabbit monoclonal Anti ENO1 | Abcam | WB - 1:5000 | ab155102 |
| Rabbit monoclonal Anti HSP60 | Abcam | WB - 1:2000 | ab190828 |
| Rabbit monoclonal GRP78 | Abcam | WB - 1:2000 | ab108615 |
| Mouse monoclonal anti HSP70 | Abcam | WB - 1:2000 | ab2787 |
| Rabbit polyclonal anti RPS3 | Millipore | WB - 1:1000 | ABE391 |
| Rabbit monoclonal anti RPL26 | Abcam | WB - 1:2000 | ab18110 |
| mouse monoclonal anti eEF1A | Millipore | WB - 1:1000 | 2787685 |
| Rabbit Ribosomal protein S6 | Cell Signaling Technology | WB - 1:1000 | 2211S<br>4858S |
| Rabbit Ribosomal protein pS6 (235/236) | Cell Signaling Technology | WB - 1:1000 | 4858S |
| Mouse Actin Beta | Sant Cruz | WB - 1:1000 | Sc-69879 |

HRP-conjugated secondary antibodies were purchased from Santa Cruz Biotechnology (used at 1:10,000 dilution, catalog no. sc-2004, catalog no. sc-2005), while Streptavidin-HRP (Trascendent kit, catalog no. L5080, used at 1:1,000 dilution) was purchased from Promega. The chemiluminescence was acquired by ChemDoc-It (Bio-Rad) and analyzed with ImageJ software (v 1.45s). Precision Plus Protein Standard Kaleidoscope standard (Biorad catalog no. 161-0375) or PageRuler Prestained Protein Ladder (Termo Fisher, catalog no. 26617) was used as ladder protein marker.

Polysome Profiling

Cells were incubated for 5 minutes with cycloheximide 10 µg/mL at 37° C. to trap the ribosomes on the mRNAs. Cells were then washed with PBS complemented with cycloheximide (10 µg/mL) and scraped directly on the plate with 300 µL of lysis buffer (10 mM NaCl, 10 mM $MgCl_2$, 10 mM Tris-HCl, pH 7.5, 1% Triton X-100, 1% sodium deoxycholate, 0.2 U/mL, 5 U/mL DNAse I, 200 U/mL RNase inhibitor, and 10 µg/mL cycloheximide, protease inhibitor). Nuclei and cellular debris were removed by three consecutive centrifugations (800 g, 5 min at 4° C.). The supernatant was directly transferred onto a 15-50% linear sucrose gradient containing 100 mM NaCl, 10 mM $MgCl_2$, 30 mM Tris-HCl, pH 7.5 and centrifuged in a Sorvall ultracentrifuge on a swinging rotor for 100 min at 180,000 g at 4° C. The fraction corresponding to the 40S, 60S and 80S peaks and those corresponding to polysomes were collected monitoring the absorbance at 254 nm. Each fraction was flash frozen in liquid nitrogen and stored at −80° C. for protein extraction.

Immunoprecipitation

For Immunoprecipitation, cells were harvested with lysis buffer (10 mM NaCl, 10 mM $MgCl_2$, 10 mM Tris-HCl, pH 7.5, 1% Triton X-100, 1% sodium deoxycholate, 0.2 U/mL, 5 U/mL DNAse I, 200 U/mL RNase inhibitor, and 10 µg/mL cycloheximide, protease inhibitor) and precleared with protein A/G Magnetic Agarose beads (Thermo Scientific, catalog no. 78609) for 30 min at 4 C. The precleared lysates were incubated with specific antibodies against p-RPS6 (235/236), puromycin and IgG controls respectively for 1 hour at 4° C. in buffer 10 mM HEPES pH-7.5, 150 mM KCl, 5 mM $MgCl_2$, 100 ug/ml CHX. Protein A/G magnetic agarose beads (50 µl, Thermo) were added to individual samples and incubated for 1 hour at 4° C. The beads were then washed intensively with wash buffer (10 mM HEPES pH-7.5, 350 mM KCl, 5 mM $MgCl_2$, 0.05 M DTT, 1% NP40, 100 ug/ml CHX) on ice. After the final wash beads were transferred to new vials and boiled with 6× Laemmeli loading buffer for 10 min at 95° C. and resolved on SDS polyacrylamide gel followed by Immunoblotting as described above.

Immunofluorescence

MCF7 cells were grown to 80% of confluence and treated with CHX (10 µg/mL, 5 min, 37° C.) and probe (10 min, 37° C.). Cells were washed thrice with cold PBS (containing CHX 10 µg/mL), placed on ice and irradiated under a UV lamp at 365 nm for 5 min (0.75 $J/cm^2$) followed by washing twice with PBS. Subsequently, cells were fixed with 4% formaldehyde in PBS for 15 min on a coverslip and permeabilized with ice cold 100% methanol for 10 min at −20° C. Post permeabilization, cells were washed twice with PBS and incubated with 1 ml "click" buffer (PBS containing picolyl azide sulfo cy3, 0.02 mM $Cu^{++}$, 0.5 mM ascorbic acid) for 1 hour at room temperature. Cells were blocked with blocking buffer (5% BSA, 0.3% triton×100 in PBS) for 1 hour and incubated with (i) the indicated primary antibody (1:200) and then with (ii) the secondary antibody (1:3000) in 3% BSA, 0.2% saponin, 2.5% vol/vol polyvinyl sulfonic acid, 40 U/ml RNase inhibitor. Finally, after washing thrice with PBS the slides were mounted with ProLong Gold Antifade (Invitrogen, Catalog no P36962) and viewed using a confocal microscope.

Confocal Microscopy

Laser scanning confocal microscopy (LSCM) analysis was carried out using a Leica DM6000CD microscope equipped with an argon laser source. MCF7 cells were immunostained with RPL26 or HSC-70 FITC (Ex. 492 nm, Em. 519 nm) and 3PB/3PBis-Cy3 (Ex. 552 nm, Em. 578 nm).

Copper Catalyzed "Click" Reaction in the Cell Lysate and Pull-Down

Cell lysates (0.35 ml) were incubated with $CuSO_4$ (2.00 µmol), picoly-PEG4-Biotin (2.00 µmol) or Picolyl azide sulfo cy 3 Jena Bioscience (catalog no. CLK-1178-1, 2.00 µmol), THPTA (10 µmol) and Sodium Ascorbate (100 µmol) overnight a 4° C. For pull-don experiments, the cell lysate was then incubated with 500 µL of MAGAR-cN (IMMAGINA BioTechnology, catalog no. 016-00-007-2-1) for 1 hour at RT.

Synthesis and Purification of 3PB-Biotin and 3PBis-Biotin

3PB or 3PBis (1.00 µmol), Azide-PEG3-Biotin (2.00 µmol), $CuSO_4$ (2.00 µmol), THPTA (10 µmol) and Sodium Ascorbate (100 µmol) were dissolved in Water-DMSO 1:1

(0.3 mL) and mixed overnight at room temperature. The final product was extracted by CHCl₃ with the aid of sonication, than the product was obtained by solvent evaporation under vacuum. The reaction was checked with MS and thin Layer Chromatography (TLC).

Beads Functionalization with 3PB/3PBis-Biotin

3PB or 3PBis were dissolved in 2M NaCl, 10 mM Tris, pH 7.5 (in DEPC water) at the final concentration of 1 mM and incubated in the same volume of MAGAR-cN beads for 1 hour. The beads were washed five times with PBS to remove the unbound 3PB/3PBis molecules.

REFERENCES

1. Ban, N., Nissen, P., Hansen, J., Moore, P. B. & Steitz, T. a. The complete atomic structure of the large ribosomal subunit at 2. 4 *A Resolut. Sci.* 289, 905±920 (2000).
2. Hansen, J. L., Schmeing, T. M., Moore, P. B. & Steitz, T. A. Structural insights into peptide bond formation. *Proc Natl Acad Sci USA* 99, 11670-11675 (2002).
3. Brandt, F. et al. The Native 3D Organization of Bacterial Polysomes. *Cell* 136, 261-271 (2009).
4. NATHANS, D. & NEIDLE, A. Structural Requirements for Puromycin Inhibition of Protein Synthesis. *Nature* 197, 1076-1077 (1963).
5. Yarmolinsky, M. B. & Haba, G. L. Inhibition By Puromycin of Amino Acid Incorporation Into Protein. *Proc. Natl. Acad. Sci. U.S.A* 45, 1721-1729 (1959).
6. Gilbert, W. Polypeptide synthesis in *Escherichia coli*: II. The polypeptide chain and S-RNA. *J. Mol. Biol.* 6, 389-403 (1963).
7. ALLEN, D. W. & ZAMECNIK, P. C. The effect of puromycin on rabbit reticulocyte ribosomes. *Biochim. Biophys. Acta* 55, 865-874 (1962).
8. Liu, J., Xu, Y., Stoleru, D. & Salic, A. Imaging protein synthesis in cells and tissues with an alkyne analog of puromycin. *Proceedings of the National Academy of Sciences* 109, 413-418 (2012).
9. Ge, J. et al. Puromycin Analogues Capable of Multiplexed Imaging and Profiling of Protein Synthesis and Dynamics in Live Cells and Neurons. *Angew. Chemie Int. Ed.* n/a-n/a (2016). doi:10.1002/anie. 201511030
10. Aviner, R., Geiger, T. & Elroy-Stein, O. Genome-wide identification and quantification of protein synthesis in cultured cells and whole tissues by puromycin-associated nascent chain proteomics (PUNCH-P). *Nat. Protoc.* 9, 751-60 (2014).
11. Schmeing, T. M. et al. A pre-translocational intermediate in protein synthesis observed in crystals of enzymatically active 50S subunits. *Nat Struct Biol* 9, 225-230 (2002).
12. Simsek, D. et al. The Mammalian Ribo-interactome Reveals Ribosome Functional Diversity and Heterogeneity. *Cell* 169, 1051-1065.e18 (2017).
13. Aviner, R. et al. Proteomic analysis of polyribosomes identifies splicing factors as potential regulators of translation during mitosis. *Nucleic Acids Res.* 45, 5945-5957 (2017).
14. Wang, M. et al. Essential role of the unfolded protein response regulator GRP78/BiP in protection from neuronal apoptosis. *Cell Death Differ.* 17, 488-498 (2010).
15. Laitusis, A. L., Brostrom, M. A. & Brostrom, C. O. The dynamic role of GRP78/BiP in the coordination of mRNA translation with protein processing. *J. Biol. Chem.* 274, 486-493 (1999).
16. Luo, S., Mao, C., Lee, B. & Lee, A. S. GRP78/BiP Is Required for Cell Proliferation and Protecting the Inner Cell Mass from Apoptosis during Early Mouse Embryonic Development. *Mol. Cell. Biol.* 26, 5688-5697 (2006).
17. Wey, S. et al. Inducible knockout of GRP78/BiP in the hematopoietic system suppresses Pten-null leukemogenesis and AKT oncogenic signaling. *Blood* 119, 817-825 (2012).
18. Gulow, K., Bienert, D. & Haas, I. G. BiP is feed-back regulated by control of protein translation efficiency. *J. Cell Sci.* 115, 2443-52 (2002).
19. Ni, M., Zhou, H., Wey, S., Baumeister, P. & Lee, A. S. Regulation of PERK signaling and leukemic cell survival by a novel cytosolic isoform of the UPR regulator GRP78/BiP. *PLoS One* 4, (2009).
20. Albanese, V., Yam, A. Y. W., Baughman, J., Parnot, C. & Frydman, J. Systems analyses reveal two chaperone networks with distinct functions in eukaryotic cells. *Cell* 124, 75-88 (2006).
21. Doring, K. et al. Profiling Ssb-Nascent Chain Interactions Reveals Principles of Hsp70-Assisted Folding. *Cell* 170, 298-311.e20 (2017).
22. Liu, B., Han, Y. & Qian, S. B. Cotranslational Response to Proteotoxic Stress by Elongation Pausing of Ribosomes. *Mol. Cell* 49, 453-463 (2013).
23. Kambe, T., Correia, B. E., Niphakis, M. J. & Cravatt, B. F. Mapping the protein interaction landscape for fully functionalized small-molecule probes in human cells. *J. Am. Chem. Soc.* 136, 10777-10782 (2014).
24. Rostovtsev, V. V, Green, L. G., Fokin, V. V & Sharpless, K. B. A stepwise huisgen cycloaddition process: copper (I)-catalyzed regioselective 'ligation' of azides and terminal alkynes. *Angew. Chem. Int. Ed. Engl.* 41, 2596-9 (2002).
25. Schmidt, E. K., Clavarino, G., Ceppi, M. & Pierre, P. SUnSET, a nonradioactive method to monitor protein synthesis. *Nat. Methods* 6, 275-277 (2009).
26. Casas, C. GRP78 at the centre of the stage in cancer and neuroprotection. *Front. Neurosci.* 11, 1-15 (2017).
27. Ni, M., Zhang, Y. & Lee, A. S. Beyond the endoplasmic reticulum: atypical GRP78 in cell viability, signalling and therapeutic targeting. *Biochem. J.* 434, 181-188 (2011).
28. Nakai, A. et al. Expression and phosphorylation of BiP/GRP78, a molecular chaperone in the endoplasmic reticulum, during the differentiation of a mouse myeloblastic cell line. *Cell Struct. Funct.* 20, 33-9 (1995).
29. MacIas, A. T. et al. Adenosine-derived inhibitors of 78 kDa glucose regulated protein (Grp78) ATPase: Insights into isoform selectivity. *J. Med. Chem.* 54, 4034-4041 (2011).
30. Evans, L. E., Jones, K. & Cheeseman, M. D. Targeting secondary protein complexes in drug discovery: studying the druggability and chemical biology of the HSP70/BAG1 complex. *Chem. Commun.* 53, 5167-5170 (2017).
31. Cheeseman, M. D. et al. Exploiting Protein Conformational Change to Optimize Adenosine-Derived Inhibitors of HSP70. *J. Med. Chem.* 59, 4625-4636 (2016).
32. Hughes, S. J. et al. Probing the ATP Site of GRP78 with 55 Nucleotide Triphosphate Analogs. *PLoS One* 11, e0154862 (2016).
33. Knight, Z. A. et al. Molecular Profiling of Activated Neurons by Phosphorylated Ribosome Capture. *Cell* 151, 1126-1137 (2012).

The invention claimed is:
1. A chemical compound having the structural formula (I):
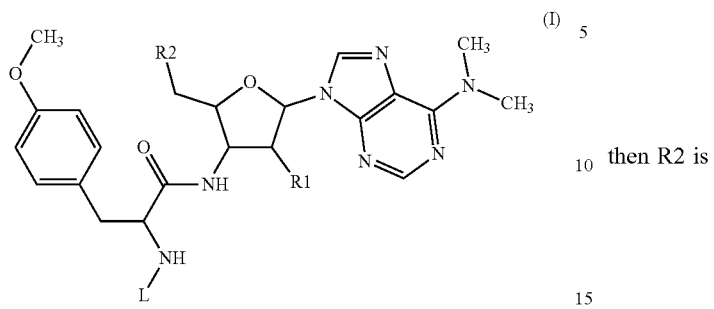
wherein
R1 and R2 are independently selected from
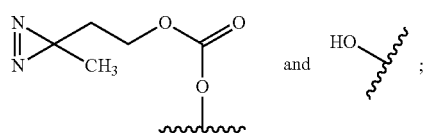
L is selected from
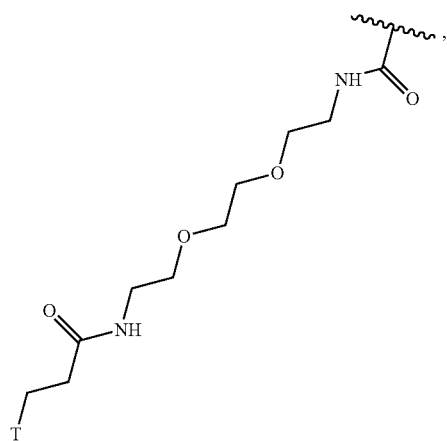
T is selected from
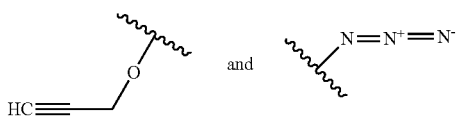
with the proviso that
if R1 is
then R2 is
2. The chemical compound according to claim 1, wherein R1 is
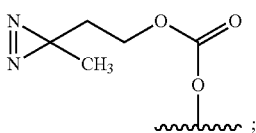 [SMILES: *OC(=O)OCCC1(C)N=N1]
R2 is selected from
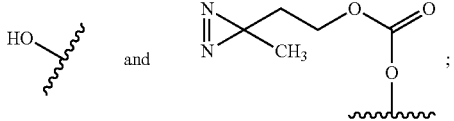
and
L is
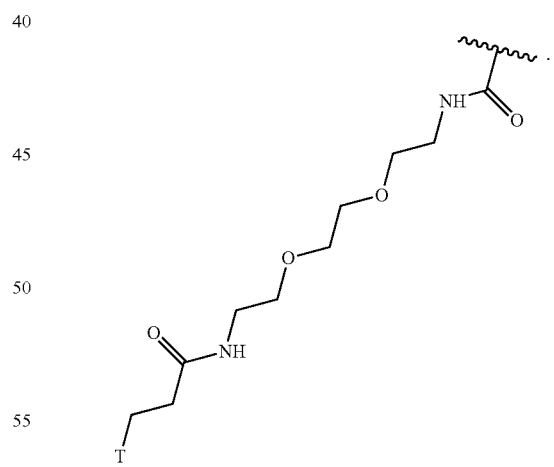
3. The chemical compound according to claim 2, wherein T is
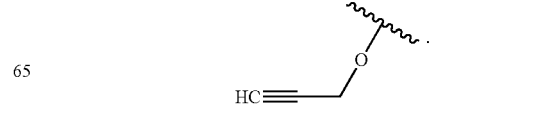

4. The chemical compound according to claim 1, wherein R1 and R2 are

and
L is selected from

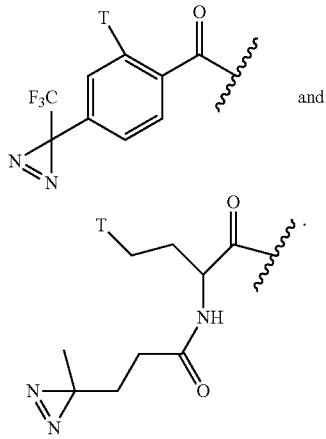

5. The chemical compound according to claim 4, wherein L is

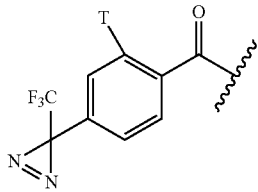

and T is

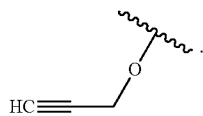

6. The chemical compound according to claim 4, wherein L is

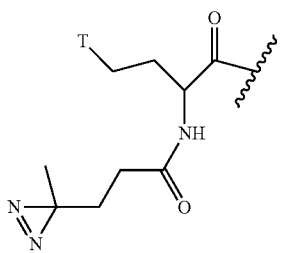

and T is

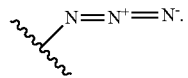

7. A method for targeting a translating ribosome, a ribosome-interacting protein, or a protein associated to a nascent polypeptide emerging, during its translation, from a ribosome in a biological sample comprising the following steps: (i) putting in contact a chemical compound of claim 1 with the biological sample, (ii) exposing the biological sample and the chemical compound to UV irradiation so that the chemical compound binds to the translating ribosome, the ribosome-interacting protein or the protein associated to a nascent polypeptide emerging from the ribosome forming a complex, and (iii) detecting the chemical compound bound to the translating ribosome, the ribosome-interacting protein or the protein associated to a nascent polypeptide emerging from the ribosome.

8. The method according to claim 7, wherein before step (iii) a purification step of the complex from the biological sample is carried out.

9. The method according to claim 8, wherein the purification step of the complex is carried out by separating the complex from the biological sample by means of coupling the complex with a bead, wherein the bead includes an azide moiety bound to its surface able to react with the alkyne group present in the chemical compound.

10. The method according to claim 8, wherein the translating ribosome is associated to an RNA, and the purification step of a complex comprising the translating ribosome and the chemical compound is carried out by means of RNA extraction followed by coupling the RNA bound to the chemical compound with a bead, wherein the bead includes an azide moiety bound to its surface able to react with the alkyne group present in the chemical compound.

11. The method according to claim 7, wherein the detection step (iii) is carried out by means of immunoblot, mass-spectroscopy, RNA sequencing or detection of light emission from a fluorescent molecule comprising an azide moiety able to react with the alkyne group present in the chemical compound or a luminescent molecule binding a biotin molecule comprising an azide moiety able to react with the alkyne group present in the chemical compound.

12. The method according to claim 11, wherein the immunoblot is carried out by means of an anti-puromycin antibody.

13. The method according to claim 7, wherein the translating ribosome is associated to an RNA, or a protein.

14. The method according to claim 13, comprising a further step (iv) of identification of the ribosome-associated RNA, the ribosome-associated protein, the ribosome-interacting protein or the protein associated to a nascent polypeptide emerging from the ribosome bound with the chemical compound.

15. The method according to claim 14, wherein the identification is carried out by means of immunoblot, mass-spectroscopy, or RNA sequencing.

16. The method according to claim 13, wherein the ribosome-associated RNA is selected from rRNA, non-coding RNA and mRNA.

17. The method according to claim 7, wherein the biological sample is selected from a cell culture, a cell lysate and a tissue lysate.

18. The method according to claim 7, wherein the ribosome interacting protein is selected from the following families: elongation factors, chaperon proteins, ribosomal proteins, proteins involved in cell metabolism, RNA processing proteins, proteins part of cytoskeleton.

19. A process of monitoring protein synthesis comprising labelling a translating ribosome, a ribosome-interacting protein, or a protein associated to a nascent polypeptide emerging, during its translation, from a ribosome in a biological sample with a chemical compound of claim 1.

20. The process of claim 19, wherein the labelling comprises UV irradiation of the chemical compound of claim 1 to form a covalent link between the chemical compound of claim 1 and the translating ribosome, ribosome-interacting protein, or protein associated to the nascent polypeptide.

21. The process of claim 19, further comprising detecting the labeled translating ribosome, ribosome-interacting protein, or protein associated to the nascent polypeptide.

22. The process of claim 19, further comprising separating the labeled translating ribosome, ribosome-interacting protein, or protein associated to the nascent polypeptide.

23. The process of claim 22, wherein the separating comprises coupling the labeled translating ribosome, ribosome-interacting protein, or protein associated to the nascent polypeptide with a reporter tag through an alkyne azide reaction.

24. The process of claim 23, further comprising detecting the labeled translating ribosome, ribosome-interacting protein, or protein associated to the nascent polypeptide that has the reporter tag.

25. The process of claim 19, further comprising identifying the labeled translating ribosome, ribosome-interacting protein, or protein associated to the nascent polypeptide.

26. The process of claim 19, wherein the translating ribosome is associated with an RNA or a protein.

* * * * *